US008802848B2

(12) United States Patent
Dicke et al.

(10) Patent No.: US 8,802,848 B2
(45) Date of Patent: Aug. 12, 2014

(54) MELAMINE BASED MANNICH-COMPOUNDS AND A PROCESS FOR OBTAINING THE SAME

(75) Inventors: René Dicke, Leonding (AT); Christoph Hahn, Linz (AT); Martin Burger, Traunstein (DE); Andreas Endesfelder, Overath (DE); Katarina Rot, Leonding (AT); Clemens Schwarzinger, Wels (AT); Klaus Bretterbauer, Linz (AT); Heinrich Trischler, Linz (AT); Harald Schmidt, Linz (AT)

(73) Assignee: Borealis Agrolinz Melamine GmbH, Linz (AT)

( * ) Notice: Subject to any disclaimer, the term of this patent is extended or adjusted under 35 U.S.C. 154(b) by 12 days.

(21) Appl. No.: 13/511,164

(22) PCT Filed: Nov. 17, 2010

(86) PCT No.: PCT/EP2010/067671
§ 371 (c)(1),
(2), (4) Date: Jul. 18, 2012

(87) PCT Pub. No.: WO2011/061220
PCT Pub. Date: May 26, 2011

(65) Prior Publication Data
US 2012/0277429 A1 Nov. 1, 2012

(30) Foreign Application Priority Data

Nov. 23, 2009 (EP) ..................... 09176756
Dec. 16, 2009 (EP) ..................... 09179461

(51) Int. Cl.
*C07D 251/64* (2006.01)
*C07D 251/70* (2006.01)
*C08G 12/32* (2006.01)

(52) U.S. Cl.
CPC ............ *C07D 251/64* (2013.01); *C07D 251/70* (2013.01); *C08G 12/32* (2013.01)
USPC ........... 544/196; 544/197; 544/200; 528/254; 528/243

(58) Field of Classification Search
CPC ..... C07D 251/64; C07D 251/70; C08G 12/32
USPC ................... 544/196, 197, 200; 528/254, 243
See application file for complete search history.

(56) References Cited

U.S. PATENT DOCUMENTS 6,780,511 B2 * 8/2004 Gerber .................. 428/414
2006/0194803 A1 8/2006 Kubota et al.

FOREIGN PATENT DOCUMENTS

EP 1479397 A1 11/2004
WO 03032903 A2 4/2003
WO 2009028891 A2 3/2009

OTHER PUBLICATIONS

Mannich, "Eine Synthese von β-Ketonbasen", Eingegangen den, 1917, p. 261, vol. 80—IV.
Braun et al., "Gemeinsame Kondensation von Phenol, Melamin und Formaldehyd", Die Angewandte Makromolekulare Chemie, 1982, pp. 141-159, vol. 108.
Braun et al., "Gemeinsame Kondensation von Phenol, Melamin und Formaldehyd", Die Angewandte Makromolekulare Chemie, 1984, pp. 9-26, vol. 125.
Braun et al., "Gemeinsame Kondensation von Phenol, Melamin und Formaldehyd", Die Angewandte Makromolekulare Chemie, 1984, pp. 27-36, vol. 125.
Maciejewski et al., "Highly branched melamine-phenollic novolaks", Polymer Bulletin, 2002, pp. 251-259, vol. 48.
Diem et al., "Amino Resins", 2005, pp. 1-29, Wiley-VCH Verlag GmbH & Co. KGaA, Weinheim, Germany.
Bujnowski et al., "o-Aminomethylderivatives of phenols. Part 3. Mechanistic investigation of a Mannich reaction of phenols with N-methylenealkylamines", ARKIVOC, 2008, pp. 106-114, vol. xiii.
Rima et al., "New spectrophotometric method for the quantitative determination of melamine using Mannich reaction", Journal of Food Composition and Analysis, 2009, pp. 689-693, vol. 22.
Fu, Shen-Yuan et al., "Copolymerization mechanism and properties of melamine-phenol-formaldehyde resin", Journal of Beijing Forestry University, vol. 30, No. 3, 2008, pp. 107-112. (English-Language Abstract Included).

* cited by examiner

*Primary Examiner* — Venkataraman Balasubramanian
(74) *Attorney, Agent, or Firm* — The Webb Law Firm

(57) ABSTRACT

The present invention relates to Melamine based Mannich compounds of the general formulae (1)-(12) and a process for synthesizing melamine based Mannich-products comprising the steps of a) reacting at least one substituted melamine with at least one aldehyde, in particular formaldehyde, under basic conditions to form at least one OH-containing compound, b) reacting the at least one OH-containing compound in the presence of a catalyst to form at least one mannich-base, c1) reacting the at least one mannich-base with at least one enol-forming carbonyl compound, or c2) reacting the at least one mannich-base with at least one aromatic compound, and d) working up the reaction mixture. The invention relates further to precondensates obtainable from these products.

25 Claims, 3 Drawing Sheets

MELAMINE BASED MANNICH-COMPOUNDS AND A PROCESS FOR OBTAINING THE SAME

CROSS-REFERENCE TO A RELATED APPLICATION

This application is a National Phase Patent Application of International Patent Application Number PCT/EP2010/067671, filed on Nov. 17, 2010, which claims priority of European Patent Application Number 09176756.6, filed on Nov. 23, 2009 and of European Patent Application Number 09179461.0, filed on Dec. 16, 2009.

BACKGROUND

The present invention relates to Melamine based Mannish compounds, a process for obtaining the same, precondensation products and their uses.

Monomers based on melamines and phenols are interesting building blocks for the synthesis of resins (Ullmans encyclopedia of Industrial Chemistry, 2005, 6$^{th}$ ed).

Melamine-based resins are usually obtained from polymerization of melamines and aldehydes, in particular formaldehyde. The degree of polymerisation is adjustable by the applied reaction conditions, such as temperature, pH-value, catalysts or fillers. Melamine pre-condensates can be etherified and used as surface coating resins. Melamine-formaldehyde resins are mixable with alkyd resins, acrylates and epoxide resins. In the presence of saturated polyesters they cure at room temperature. Melamine resins are widely applicable in particular for the production of laminates, electrically isolating material, glues for paper or the wood industry and others.

Phenol based resins are obtained by condensation of phenols and formaldehydes. Two types are distinguishable: novolak and resol. Novolak is synthesized in an acidic reaction media with a stoichiometric deficiency of formaldehyde. The non-hardened products are crosslinked in the presence of hardeners. Resol on the other side are obtained in an alkali- or basic media with an excess of formaldehyde. Novolak and resol have a good stability, stiffness, stress crack resistance and hardness. They are mainly used as glues for wood and wood fibres, for insulating material, hard paper or as binders. A drawback of phenol based resins is their yellowish till brownish colour and their instability in the presence of strong acids and bases.

Different attempts have been carried out to combine the properties of melamine and phenole based resins. As one approach different reactions conditions for a combined condensation of phenol, melamine and formaldehyde were tested (Braun and Ritzert, Angewandte Makromol. Chemie, 1984, 125: 9-26). By varying pH-value and the molar ratio the authors were able to show that neither under acidic conditions nor basic conditions a co-condensation of melamine, phenol and formaldehyde occurred. This is due to the different pH-depenndet reaction mechanism: the reactivity of phenol towards formaldehyde is highest in the basic milieu whereas the reactivity of melamine is highest in the acidic reaction milieu. Any products obtained by a simultaneous reaction of phenol, melamine and formaldehyde have to interpreted as interpenetrating networks of phenol resins and melamine resins (Braun and Ritzert, Angewandte Makromol. Chemie, 1984, 125: 27-36).

The Mannich reaction [Mannich C, 1917, Arch Pharm. 255, 261-276] is well known. The Mannich-reaction comprises the condensation of an aldehyde, preferably formaldehyde, with ammonia, a primary or secondary amine under formation of an imminium-ion which undergoes a reaction with an enol-forming carbonyl compound like an aldehyde or ketone. The reaction mechanism is similar to an aldol condensation whereby the enol attacks a C=N double bond instead of a carbonyl bond.

Bujnowski et al. (Akrivoc, 2008, 106-114) describes a Mannich reaction of phenol, formaldehyde and hexahydro-1,3,5-triazine. The reactivity of this hexahydrotriazine is close to that of an aliphatic amine, so that it reacts in a Mannich-type reaction.

Aminotriazine structures that are similar to melamines have been used for the synthesis of compounds comprising a phenol derivative and a triazine (WO 03/032903). However, cyanuric chloride has been used as starting material to synthesize the aminotriazine structures.

Several attempts haven been made in the past to use melamine in a Mannich reaction.

For instance suggests Rima at el. (J. of Food Composition and Analysis, 2009, 22:689-693) a reaction of melamine with uranine in formaldehyde solution in a Mannich-type manner. Interestingly, the hypothesized Mannich-product is formed without the addition of any acid.

Maciejewski et al. (Polymer Bulletin, 2002, 48:251-259) postulates the formation of a mixture of hydroxyphenylmethylmelamines based on the Mannich-reaction of methylolated melamine and an excess of phenol in the presence of stoichometric amounts of hydrochloric acid. It is suggested that the obtained product comprises five phenol units per one melamine molecule.

Even though the above references suggest the possibility of applying melamine in a Mannich-type reaction, so far no further studies have been carried out for using in particular substituted melamines as educts in a Mannich-type reaction and the further use of the obtained products for obtaining pre-condensates.

SUMMARY OF THE INVENTION

It is therefore an object of the invention to provide compounds which can be used for the synthesis of a polymer product which combines the properties of the known melamine-formaldehyde resins and other formaldehyde containing resins, in particular phenol-formaldehyde resins, whereby their properties are easily adjustable.

According to an exemplary embodiment the present Melamine based Mannich compounds have at least one of the general formulae (1) to (6)

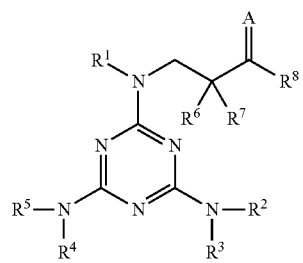

1

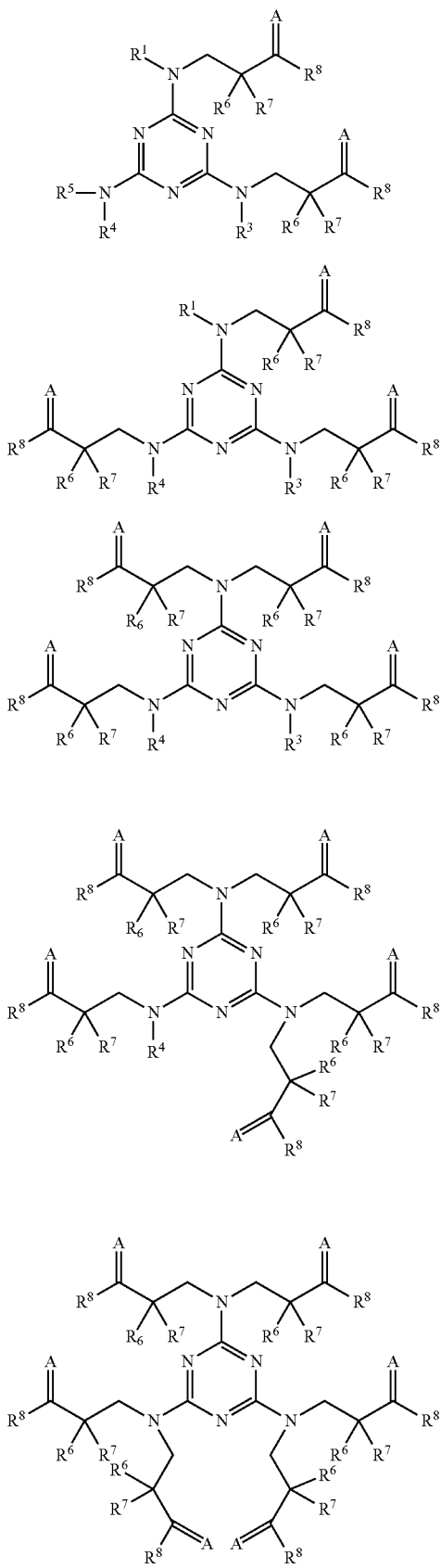

whereby

A is O, N or S the moieties $R^1$, $R^2$, $R^3$, $R^4$ and $R^5$ are selected from a group comprising H, substituted and non-substituted $C_1$-$C_{50}$-alkyl, substituted and non-substituted $C_2$-$C_{50}$-alkenyl, substituted and non-substituted $C_2$-$C_{50}$-alkinyl, substituted and non-substituted $C_3$-$C_{10}$-cycloalkyl, substituted and non-substituted $C_5$-$C_7$-cycloalkenyl, which in each case can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O— the moieties $R^6$ and $R^7$ are selected from a group comprising H, carboxyl, carboxyl ester, carboxyl amid, carboxyl halogenide, halogen, carbamate, substituted or non-substituted mercapto, substituted or non-substituted hydroxy, substituted or non-substituted amino, substituted and non-substituted carbonyl, substituted and non-substituted $C_1$-$C_{50}$-alkyl, substituted and non-substituted $C_1$-$C_{50}$-alkenyl, substituted and non-substituted $C_1$-$C_{50}$-alkinyl, whereby each alkyl, alkenyl and alkinyl chain, can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—, and the moiety $R^8$ is selected from a group comprising H, substituted or non-substituted hydroxy, substituted or non-substituted amino, halogen, substituted or non-substituted aryl, substituted or non-substituted heteroaryl, substituted and non-substituted carbonyl, substituted and non-substituted $C_1$-$C_{50}$-alkyl, substituted and non-substituted $C_1$-$C_{50}$-alkenyl, substituted and non-substituted $C_1$-$C_{50}$-alkinyl, whereby each alkyl, alkenyl and alkinyl chain, can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—.

and mixtures thereof.

It is also conceivable that the moieties $R^6$ and $R^7$ are both connected to each other in a cyclic structure. This could be for instance a cyclic ketal structure or alike.

It is furthermore conceivable that one of the moieties $R^6$ or $R^7$ and the moiety $R^8$ are part of a cyclic structure and are connected via this cyclic structure. In this case, it is imperative that the respective other moiety $R^6$ or $R^7$ is absent. The cyclic structure can be a non-substituted or further substituted $C_4$-$C_{12}$ cycloalkyl, $C_4$-$C_{12}$ cycloalkenyl moiety or a heterocyclic system.

In case, one of the moieties $R^6$ or $R^7$ and the moiety $R^8$ are part of a cyclic structure, it is to be understood that the following compound

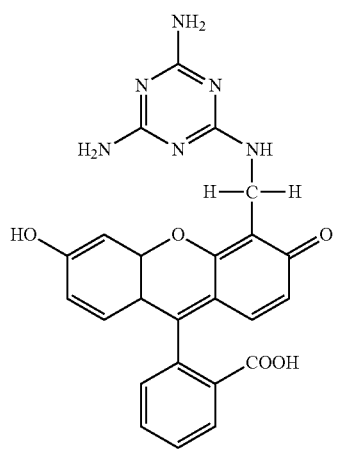 [SMILES: Nc1nc(N)nc(NCC2=C3OC4C=C(O)C=CC4C(c4ccccc4C(=O)O)=C3C=CC2=O)n1]

is exempt from the above group of Mannich-compounds of the general formulae (1) and thus disclaimed.

The cyclic structure formed by $R^6$ or $R^7$ and $R^8$ can also be of an aromatic structure, if A is present in its tautomeric AH form. Accordingly, the present compounds solving the object of the invention are also of one the following general formulae (7) to (12)

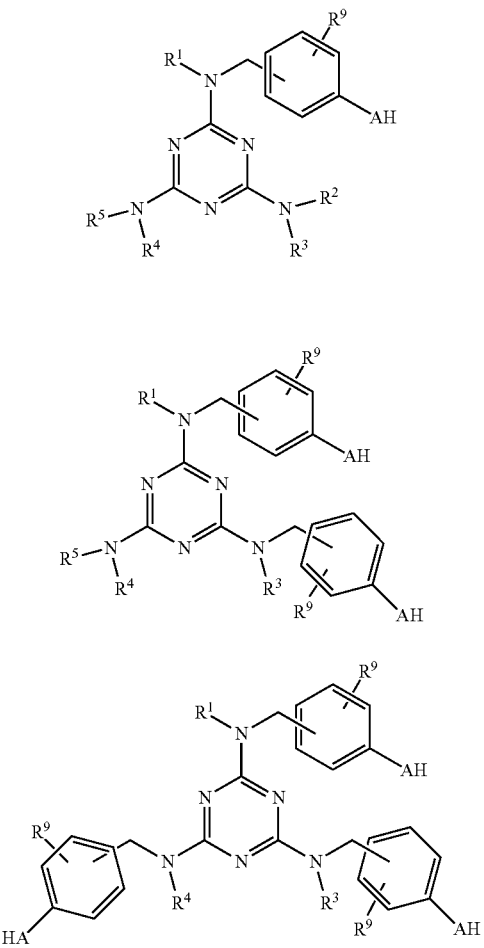

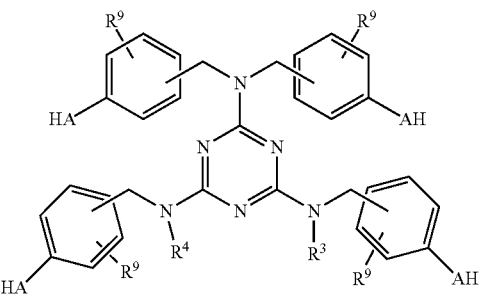

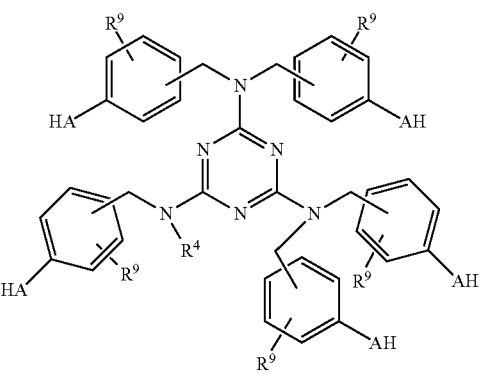

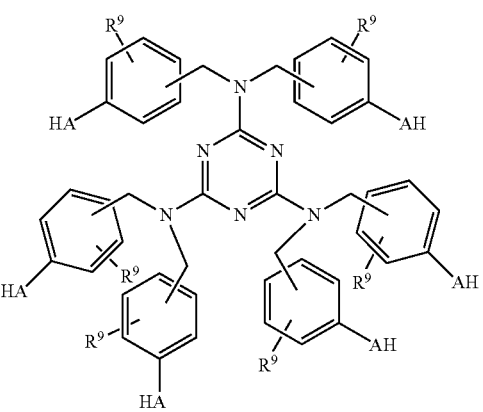

whereby

A is O, N or S the moieties $R^1$, $R^2$, $R^3$, $R^4$ and $R^5$ are selected from a group comprising H, substituted and non-substituted $C_1$-$C_{50}$-alkyl, substituted and non-substituted $C_2$-$C_{50}$-alkenyl, substituted and non-substituted $C_2$-$C_{50}$-alkinyl, substituted and non-substituted $C_3$-$C_{10}$-cycloalkyl, substituted and non-substituted $C_5$-$C_7$-cycloalkenyl, which in each case can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O— the moiety $R^9$ is selected from a group comprising H, substituted or non-substituted hydroxy, substituted or non-substituted amino, halogen, substituted or non-substituted aryl, whereby the substituted aryl can be bound via at least one methylene bridge to the aromatic structure and can be in particular a group of the of the formula

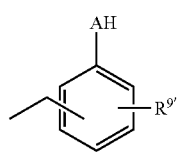

wherein $R^{9'}$ has the meaning of $R^9$, substituted or non-substituted heteroaryl, substituted and non-substituted carbonyl, substituted and non-substituted $C_1$-$C_{50}$-alkyl, substituted and non-substituted $C_1$-$C_{50}$-alkenyl, substituted and non-substituted $C_1$-$C_{50}$-alkinyl, substituted and non-substituted $C_3$-$C_{10}$-cycloalkyl, substituted and non-substituted $C_5$-$C_7$-cycloalkenyl, whereby each alkyl, alkenyl and alkinyl chain, can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—, and whereby up to four moieties R9, preferably one or two moieties R9 are present at the aromatic ring, and mixtures thereof.

It is to be pointed out that the aromatic structure —$C_6H_4R^9AH$ can be connected via the methylene group to the triazine ring in one of the general formulae (6) to (12) in any of the three possible positions to the AH-group on the aryl ring, whereby the ortho- and para-positions, e.g. ortho- and para-isomers are preferred.

It also to be understood that the compound with the following structure

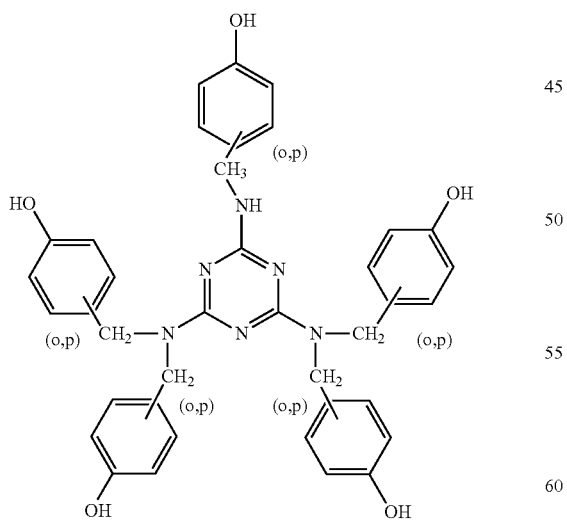

is exempt from the group of the compounds of the general formulae (6)-(12) and thus disclaimed.

In particular compounds of one of the formulae (13)-(18)

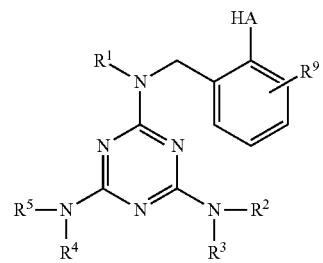

13

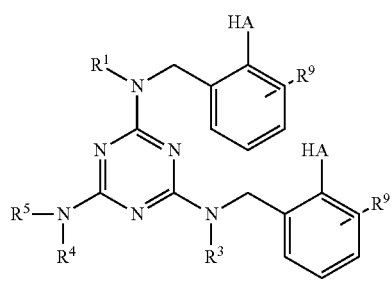

14

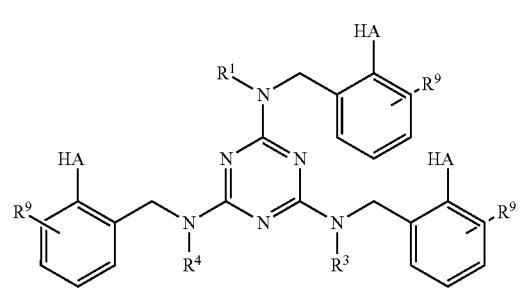

15

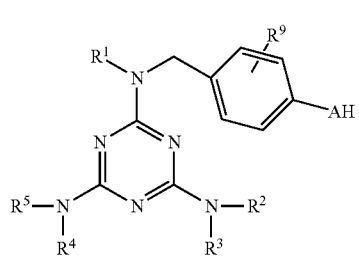

16

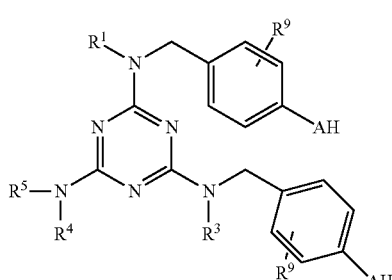

17

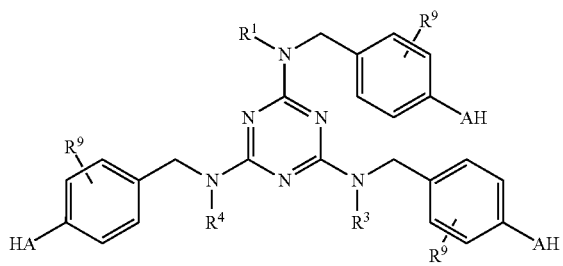

or their mixtures are preferred.

The moieties $R^1$, $R^2$, $R^3$, $R^4$ and $R^5$ can be selected from a group comprising H, substituted and non-substituted $C_1$-$C_{12}$-alkyl, substituted and non-substituted $C_3$-$C_7$-cycloalkyl and substituted and non-substituted $C_2$-$C_{12}$-alkenyl. Preferably at least one of the moieties $R^1$, $R^2$, $R^3$, $R^4$ and $R^5$ is H, methyl, ethyl, isopropyl or butyl.

The moieties $R^6$ and $R^7$ are advantageously selected from a group comprising —H, substituted and non-substituted $C_1$-$C_{12}$-Alkyl, in particular —$CH_3$, —$C_2H_5$, —$CO_2H$, —$CO_2CH_3$, —$CO_2C_2H_5$, —$COCH_3$, —$COC_2H_5$.

The moiety $R^8$ is preferably selected from a group comprising —H, —OH, substituted or non-substituted $C_1$-$C_{12}$-Alkyl, in particular —$CH_3$, —$C_2H_5$, substituted and non-substituted $C_3$-$C_7$-cycloalkyl and substituted and non-substituted $C_2$-$C_{12}$-alkenyl, substituted and non-substituted $C_6$-$C_{12}$ Aryl, in particular —$C_6H_5$.

The moiety $R^9$ is preferably selected from a group comprising —OH, —$OCH_3$, —$OC_2H_5$, —$NH_2$, substituted or non-substituted $C_1$-$C_{12}$-Alkyl, in particular —$CH_3$, —$C_2H_5$, substituted and non-substituted $C_3$-$C_7$-cycloalkyl and substituted and non-substituted $C_2$-$C_{12}$-alkenyl, substituted and non-substituted $C_6$-$C_{12}$ Aryl, in particular —$C_6H_5$, —$C_6H_4OH$, —$CH_2C_6H_5$, —$C(CH_3)_2C_6H_5$ or —$CH_2C_6H_4AH$, in particular —$CH_2$—$C_6H_4$—OH as ortho- and/or para-isomers.

The term "substituted" in connection to alkyl, alkenyl, alkinyl, cycloalkenyl relates to the substitution of one or more atoms, usually H-atoms, by one or more of the following substituents: halogen, hydroxy, protected hydroxy, oxo, protected oxo, $C_3$-$C_7$-cycloalkyl, phenyl, naphtyl, amino, protected amino, primary, secondary or tertiary amino, heterocyclic ring, imidazolyl, indolyl, pyrrolidinyl, $C_1$-$C_{12}$-alkoxy, $C_1$-$C_{12}$-acyl, $C_1$-$C_{12}$-acyloxy, nitro, carboxy, carbamoyl, carboxamid, N—($C_1$-$C_{12}$-alkyl)carboxamid, N,N-Di($C_1$-$C_{12}$-alkyl)carboxamid, cyano, methylsulfonylamino, thiol, $C_1$-$C_{10}$-alkylthio und $C_1$-$C_{10}$-alkylsulfonyl. The substituted groups can once or twice substituted with same or different substituents.

Examples for the above substituted alkyl groups comprise 2-oxo-prop-1-yl, 3-oxo-but-1-yl, cyanomethyl, nitromethyl, chlormethyl, hydroxymethyl, tetrahydropyranyloxymethy, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chlormethyl, brommethyl, iodmethyl, trifluormethyl, 6-hydroxyhexyl, 2,4-dichlor(n-butyl), 2-aminopropyl, 1-chlorethyl, 2-chlorethyl, 1-bromethyl, 2-bromethyl, 1-fluorethyl, 2-fluorethyl, 1-iodethyl, 2-iodethyl, 1-chlorpropyl, 2-chlorpropyl, 3-chlorpropyl, 1-brompropyl, 2-brompropyl, 3-brompropyl, 1-fluorpropyl, 2-fluorptopyl, 3-fluorpropyl, 1-iodpropyl, 2-iodpropyl, 3-iodpropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and alike.

Examples for the above substituted alkenylgroups comprise styrolyl, 3-chlor-propen-1-yl, 3-chlor-buten-1-yl, 3-methoxy-propen-2-yl, 3-phenyl-buten-2-yl, 1-cyanobuten-3-yl and alike.

The term "substituted" in connection to mercapto, hydroxy and amino relates to the substitution of at least one H atom by one or in case of amino up to three of one of the substituents mentioned above, in particular substituted and non-substituted $C_1$-$C_{12}$-alkyl, substituted and non-substituted $C_3$-$C_7$-cycloalkyl and substituted and non-substituted $C_2$-$C_{12}$-alkenyl. Hence, the mercapto and hydroxy group can be present as a mercaptoether or a ether group, respectively. Amino group can be present as a primary, secondary or tertiary amine.

The term "substituted" in connection to a carbonyl group relates to —COR groups whereby R can have the meaning of one of the above substituents, in particular H, substituted and non-substituted $C_1$-$C_{12}$-alkyl, substituted and non-substituted $C_3$-$C_7$-cycloalkyl and substituted and non-substituted $C_2$-$C_{12}$-alkenyl.

The term "alkinyl" as used herein relates to a moiety of the formulae R—C≡C—, in particular to a $C_2$-$C_{50}$-Alkinyl". Examples for $C_2$-$C_{50}$-alkinyle comprise ethinyl, propinyl, 2-butinyl, 2-pentinyl, 3-pentinyl, 2-hexinyl, 3-hexinyl, 4-hexinyl, 2-heptinyl, 3-heptinyl, 4-heptinyl, 5-heptinyl, octinyl, noninyl, decinyl, undecinyl, dodecinyl, as well as di- and tri-ines of straight or branched alky chains.

The term "$C_1$-$C_{12}$-alkyl" relates to moieties like methyl, ethyl, n-propyl, isopropyl, n-butyl, isobutyl, s-butyl, t-butyl, amyl, t-amyl, hexyl, heptyl, octyl, nonyl, decyl, undecyl, dodecyl, and alike. Preferred $C_1$-$C_{12}$-alkyl groups are methyl, ethyl, isobutyl, s-butyl and isopropyl.

The term "oxo" relates to a carbon atom, which is connected with an oxygen atom via a double bond whereby a keto or an aldehyde group is formed. The term "protected oxo" relates to a carbon atom, which is substituted by two alkoxy groups or is connected twice with a substituted diol forming a non-cyclic or cyclic ketal group.

The term "alkoxy" relates to moieties like methoxy, ethoxy, n-propoxy, isopropoxy, n-butoxy, t-butoxy and alike. A preferred alkoxy group is methoxy.

The term "$C_3$-$C_7$-cycloalkyl" comprises groups like cyclopropyl, cyclobutyl, cyclopentyl, cyclohexyl und cycloheptyl. The term "$C_5$-$C_7$-Cycloalkenyl" relates to a 1,2 oder 3-cyclopentenyl ring, a 1,2,3 oder 4-cyclohexenyl ring or a 1,2,3,4 or 5-cycloheptenylring.

In a preferred embodiment of the present invention the compounds have one of the following structures:

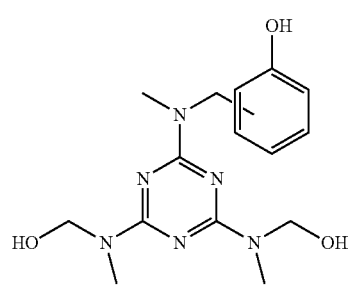

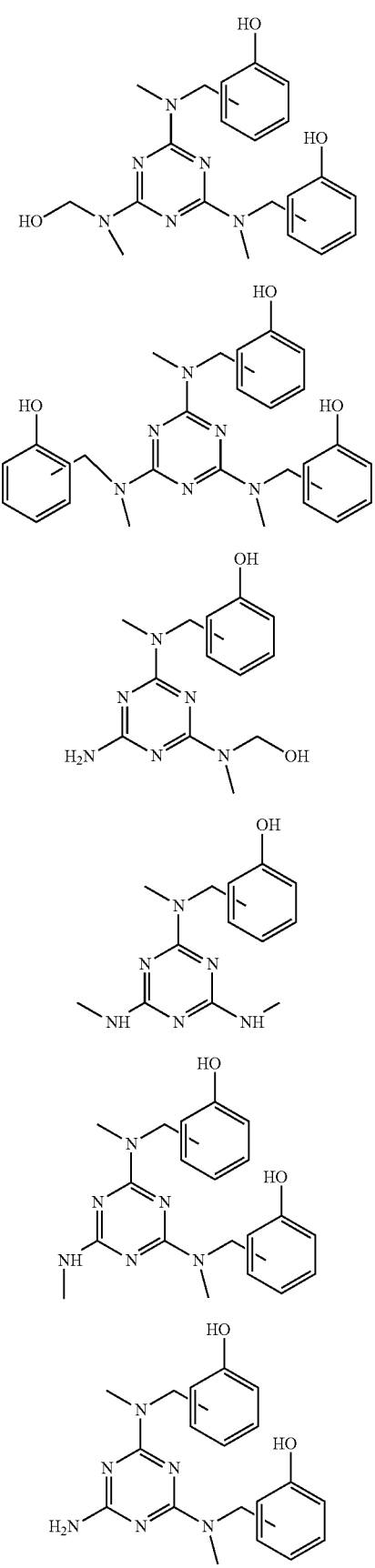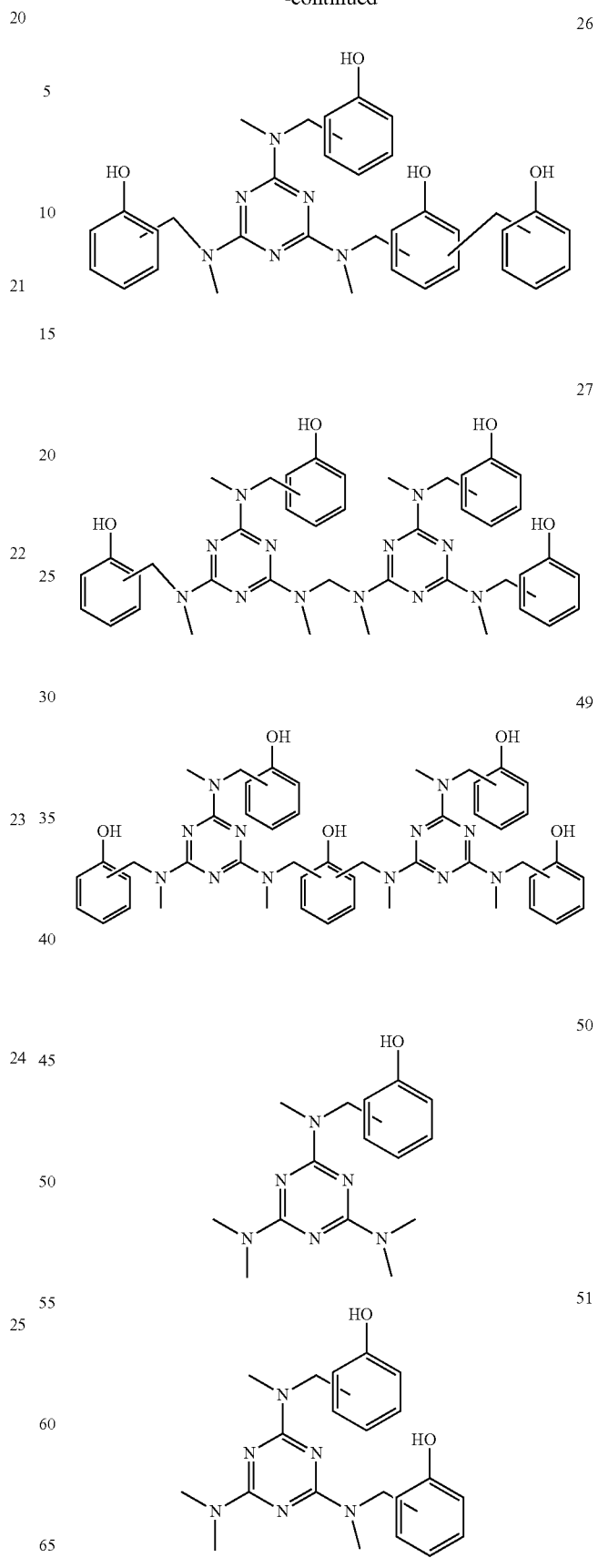

In an especially preferred embodiment the compounds have the following structures:
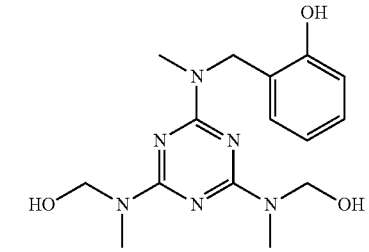
28
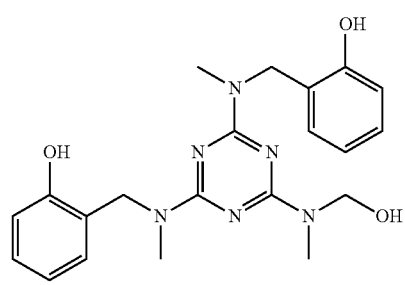
29
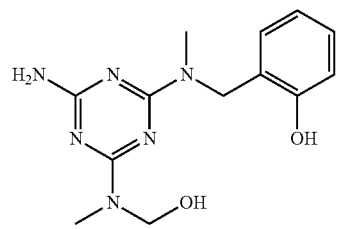
30
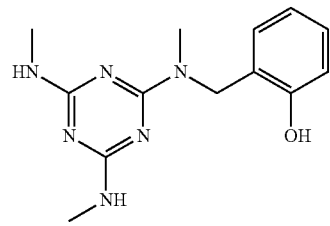
31
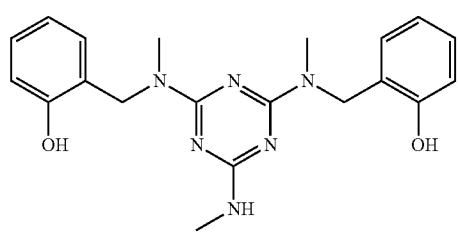
32
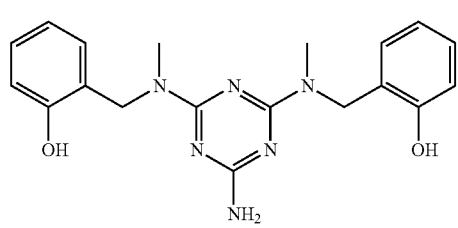
33
-continued
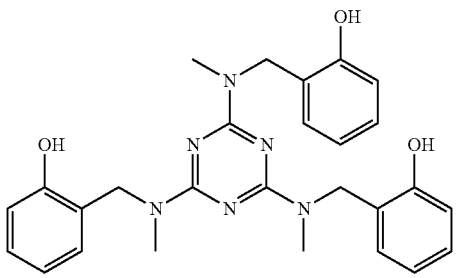
34
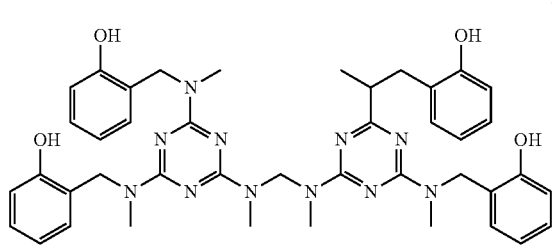
35
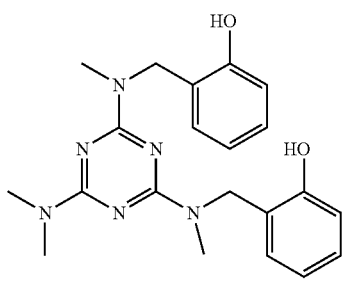
52
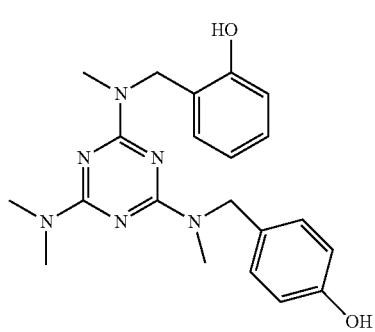
53
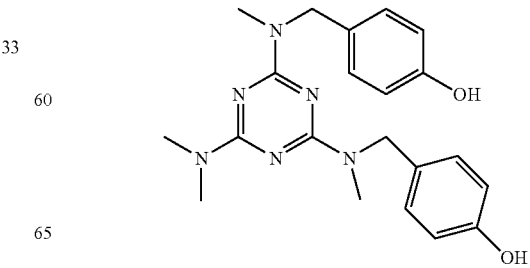
54

-continued

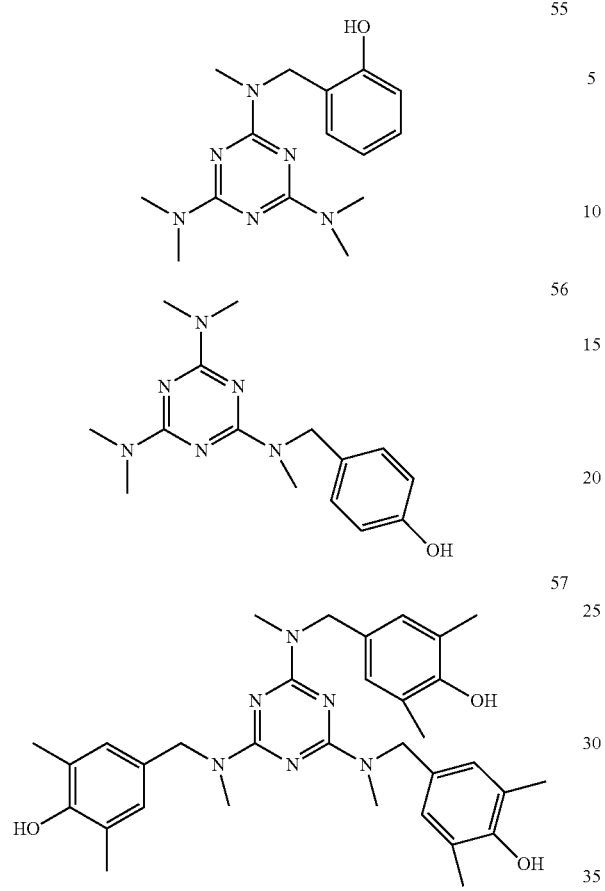

The melamine based Mannich products according to the invention, in particular the compounds comprising a phenol ring, can be also described as co-condensation products of melamine, phenol and formaldehyde. These products are especially interesting, since they are of a white colour and also do not change their appearance during further condensation.

In contrast, typical phenol resins are a dark-red to black colour.

The compounds according to the invention are obtained in a process comprising the following steps of a) reacting at least one melamine (36) with at least one aldehyde (37), in particular formaldehyde, under basic conditions to form at least one compound (38) according to the general reaction scheme I,

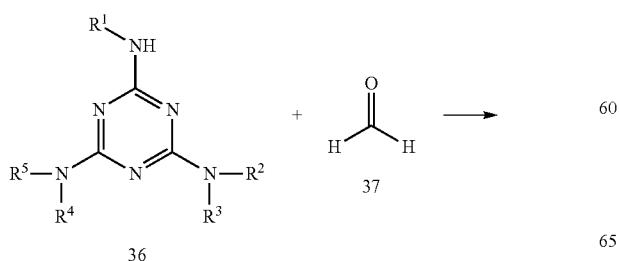

-continued

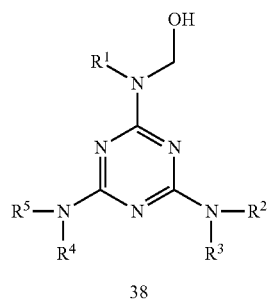

b) reacting the at least one compound (38) in the presence of a catalysts to form at least one mannich-base (39) according to the general reaction scheme II,

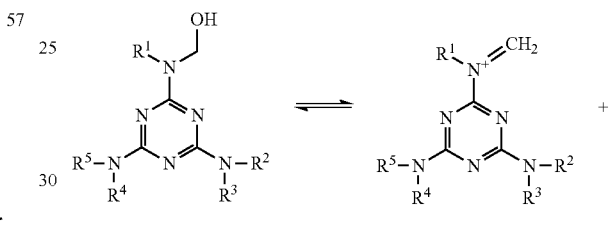

HCOOc1) reacting the at least one mannich-base (39) with at least one enol-forming carbonyl compound (40) to form at least one of the compounds according to one of the general formulae (1) to (6) according to the general reaction scheme III

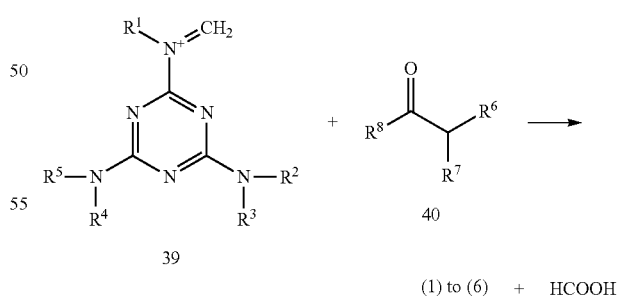

(1) to (6)  +  HCOOH or c2) reacting the at least one mannich-base (39) with at least one substituted or non-substituted aromatic compound of the general formulae (41) to form at least one of the compounds according to the general formulae (7) to (18) according to the general reaction scheme IV

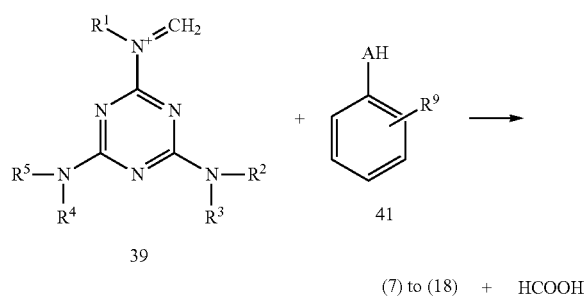

(7) to (18) + HCOOH d) and working up the reaction mixture,
whereby the moieties $R^1$, $R^2$, $R^3$, $R^4$, $R^5$, $R^6$, $R^7$, $R^8$ and $R^9$ and A have the above meanings.

In this process the formation of Iminium-ion as the mannich base in step b) is the rate-determining step. The electrophilic Iminium-ion is formed in situ by protonation of the OH-containing compound obtained in step a) followed by dehydration. In general, the Iminium-ion is stabilised in a protic polar solvent, whereas in an unpolar solvent the stability of the Iminium-ion is reduced and thus reacts faster.

It is to be understood that the process steps can be carried out in form of a one-pot synthesis or independently from each other. This means that for instance the OH-containing compounds of step a) can be are separately synthesized, isolated and stored before further usage.

The use of an alkylated melamine (36) as starting material is preferred, whereby it is in particular preferred to use an alkylated melamine with one substituent on each of the three amino groups. However, also melamine with one substituent on only two of the three amino groups or on only one of the three amino groups is applicable. It is also conceivable to apply non-substituted melamine as starting material (36).

In one embodiment of the present invention the enol-forming compound (40) is selected from a group comprising substituted and non-substitituted 1,3-bicarbonyl compounds, in particular malonic acid, acetylacetone, methylacetoacetate, acetophenone, or vinylpyrollidone.

In another preferred embodiment of the present invention the aromatic compound (41) is selected from a group comprising substituted and non-substituted phenols, in particular phenol, o-, m- or p-cresol or resorcinol, anilin, bisphenol A, bisphenol F or p-phenylphenol.

The preferred molar ratio of substituted melamine to enol-forming compound and/or aromatic compound in the process is from 6:1 to 1:6, preferably from 3:1 to 1:3, in particular preferred from 1:1 to 1:3.

In one embodiment step a) of the process is carried out at a pH between 8 and 12, preferably between 9 and 11, in the presence of an inorganic or organic base, preferably $K_2CO_3$, $Na_2CO_3$, $Ca(OH)_2$, NaOH and/or KOH.

Steps b) and c) are preferably carried out at a pH between 1-6, preferably 2 and 5, most preferably between 2 and 4.

The catalyst used in steps b), c1) or c2) is preferably selected from a group comprising sulphonic acid, sulphuric acid, trifluoracetic acid (TFAA), 4-toluenesulphonic acid (pTSA), monochloracetic acid (MCAA), glacial acetic acid, hydrochloric acid and formic acid. The molar excess of the catalyst varies dependent of the applied acid and can be between 1:10, preferably 1:5, in particular preferably 1:3, in respect to the methylolated melamine (39). However, the reaction can also be carried out using catalytic amounts of acid.

Process steps b) and c1) or c2) are carried out in a solvent or in substance. Preferably benzol, chloroform, methylenchloride, cresol, acetic acid, formic acid, formalin or water can be used as solvent.

In a preferred embodiment of the present invention acid, in particular formic acid, is used as catalyst and solvent providing Mannich compounds which underwent a three time Mannich reaction like compounds (3) or (9) in a yield up to 90%, preferably up to 80%, in particular up to 60%. The molar excess of formic acid is in this case higher and can reach an excess up to 1:20, preferably 1:15 in respect to the methylolated melamine (39).

In another preferred embodiment formaldehyde solution, in particular 35% formaldehyde solution, is added in at least one of steps b), c1) or c2) in addition to an acid as catalyst, in particular formic acid or hydrochloric acid, and the enol-forming compound (40) or the aromatic compound (41). The addition of formaldehyde at these reaction steps promotes the formation of the three times (3/3) substituted Mannich-compound of the general formulae (3) or (9) which can be obtained in a yield up to 90%, in particular 80%. Formaldehyde is added in a molar excess of 1:5, preferably 1:3 in respect to the used melamine (39). When formic acid is used as catalyst in conjunction with formalin solution then the molar excess of formic acid in respect to the methylolated melamine compound (39) is 1:40, preferably 1:30. Hydrochloride acid on the other side is preferably used in the above mentioned molar excess of 1:3.

In a further embodiment steps b) and c) are carried out in a phenol melt in the presence of nucleophilic phenolat-ions. These conditions provide especially good results, if phenol is used as the aromatic compound (41).

It is also possible to carry out steps b) and c) in the presence of a molecular sieve, preferably zeolithes. The pore size of the sieve is preferably between 3 and 10 Å. Zeolithes are known to have acidic properties and can therefore used for acid catalysed reactions. Furthermore, due to the water removing effect of the zeolithes an almost complete conversion is achieved.

It is also conceivably to combine the different reaction conditions. For instance the process can be carried out in the presence of zeolithes, an acid and/or phenol melt.

The process according to the invention enables the formation of mono-, twice and three times substituted co-condensation melamine products. Also dimers and trimers are formed.

The melamine based co-condensation products are preferably used as additives for aldehyde, in particular formaldehyde scavenging in the wood-working industry. Due to their structural elements, in particular in case of the phenolic structural element, these products are also able to react with lignin in wood, which leads to an improvement of mechanical properties of the wood and the swelling behaviour of the wood composites or particle boards.

In a further embodiment of the invention the melamine based co-condensation products are reacted with at least one aldehyde, in particular formaldehyde, acetaldehyde, furan-2-aldehyde (furfural), glyoxal, trans-3-phenyl-2-propenal (cinnamaldehyde), and giving rise to precondensates. Thus, a completely novel resin is formed.

Thus, in case of using phenol as aromatic compound (41) a hetero- or co-condensed condensed precondensate and resin comprising melamine and phenol is formed instead of interpenetrating networks of melamine and phenol resins as known from the prior art.

Such a precondensate is preferably of the following general structure

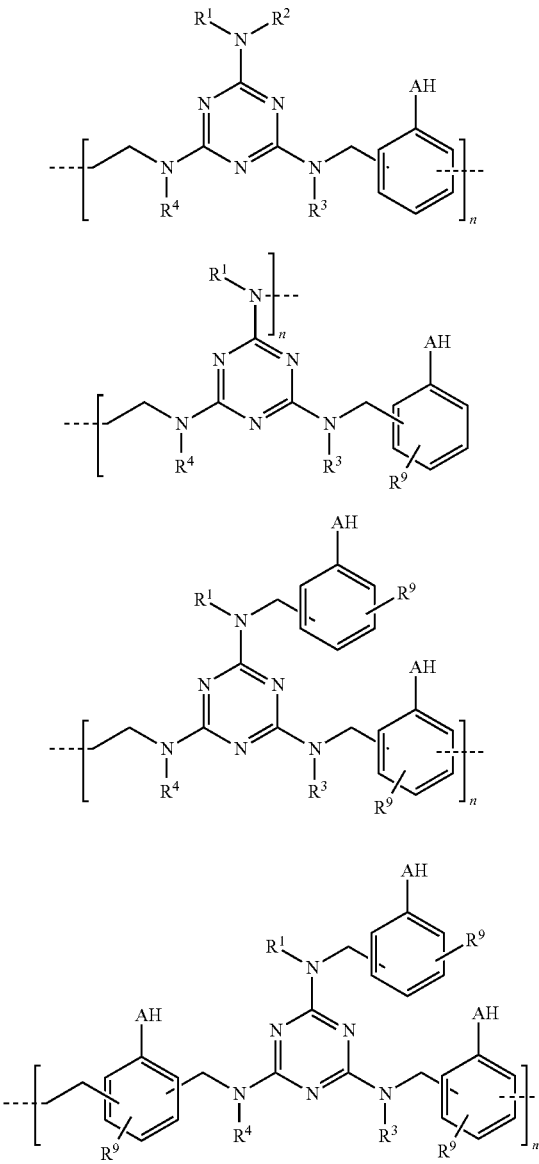

whereby n is larger than 1, preferably 1 to 50, most preferably 1 to 10.

The precondensate can be of course also be available as mixtures of different precondensates, in particular mixtures of precondensates having the above general structures (42)-(45).

Further aromatic compounds, preferably phenol and/or melamine, and/or other precondensates, preferably phenol-formaldehyde-, melamine-formaldehyde-, and/or urea-formaldehyde-precondensates, can be added to the reaction mixture of the melamine based co-condensation product and aldehyde.

Precondensates are also obtainable by mixing one of the compounds with other precondensates, preferably phenol-formaldehyde-, melamine-formaldehyde-precondensates, and/or urea-formaldehyde-precondensates.

Such obtained precondensates are preferably used for moulding compounds, laminates, glues and prepregs and as components in flame retarding systems. The precondensates can be used as cured resins in moulding compounds, in particular as covering for brakes and clutches or for commutators in electrical motors, and in laminates.

BRIEF DESCRIPTION OF THE DRAWINGS

Further advantages of the present invention will become clear on the basis of the following working examples in combination with the Figures. They show.

DETAILED DESCRIPTION OF THE INVENTION

Example 1

Figure 1:
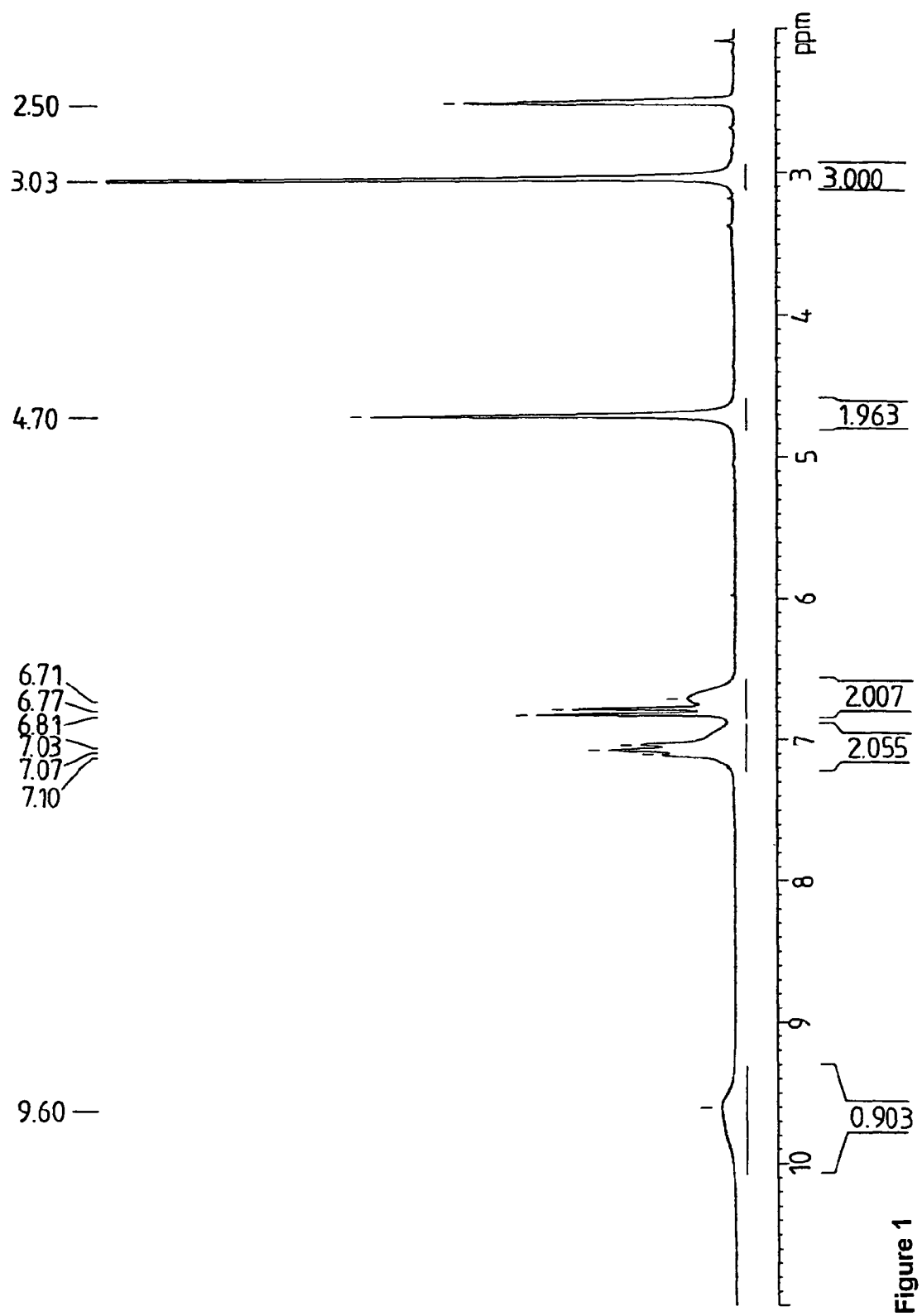
FIG. 1 a $^1$H-NMR spectra of a compound according to the invention

Mannich-Reaction in Solvent with Acid as Catalyst 0.5 g (1.9 mmole) $N^2,N^4,N^6$-tris[(trihydroxymethyl)trimethylamino]-1,3,5-triazine (Trimelamol) are provided 20 ml solvent in a 50 ml pear shaped flask. 1.66 g (19 mmole) phenol is added as a crystalline solid. The content of the flask is heated up to 45° until all educts are dissolved. 100-200 μl Acid is added. During the reaction the solution stays clear and transparent.

The reaction melt is mixed with 50 ml chloroform. The organic phase is extracted three times with 50 ml 1.5% NaOH and water. After evaporation of the organic phase a white product was obtained.

The obtained overall yield of the mannich-product differs in dependency of the used solvent, acid catalyst and pH-value (see Table 1).

TABLE 1

Experimental results of co-condensation of trimelamol and phenol in solvent and on the presence of acid

| temperature [° C.] | time [min] | yield % | catalyst | solvent |
|---|---|---|---|---|
| 25 | 360 | 46 | Formic acid, pH 2.4 | Benzene |
| 25 | 360 | 23 | acetic acid, pH 2.3 | Dioxan/Water (5:1) |
| 30 | 160 | 22 | Formic acid, pH 2.1 | Methylene chloride |
| 45 | 80 | 20 | Formic acid, pH 2.3 | Dioxan/Water (5:1) |
| 45 | 160 | 20 | Formic acid, pH 3.3 | Dioxan |
| 50 | 80 | 32 | Formic acid, pH 2.5 | Water |
| 50 | 80 | 8 | Formic acid, pH 4.5 | Acetonitrile/Water (1:1) |
| 70 | 180 | 52 | Formic acid, pH 2.8 | Benzene |
| 85 | 80 | 34 | Formic acid, pH 2 | Water |
| 90 | 80 | 42 | 18% HCl | 18% HCl |

During the reaction process the electrophilic intermediate Mannich-base and the nucleophilic phenol form a Wehland-complex, which is the rate-determining step. The complex is stabilized by suitable substituents exhibiting a +M and +I effect.

Example 2

Mannich-Reaction in Phenol Melt 0.5 g (1.9 mmole) Trimelamol are provided in a 50 ml pear shaped flask. 1.66 g (19 mmole) phenol are added as a crystalline solid. The content of the flask is heated up to 45° until all educts are dissolved in the liquid phenol. During the reaction the solution stays clear and transparent.

The reaction melt is mixed with 50 ml chloroform. The organic phase is extracted three times with 50 ml 1.5% NaOH and water. After evaporation of the organic phase a white product was obtained.

As shown in Table 2 the reaction yield and the product distribution of mono(1/1)-, bi(2/1)- and tri(3/1)-substituted mannich-products as well as the rate of dimmer/trimer formation are strongly influenced by the reaction temperature.

TABLE 2

Experimental results of co-condensation of trimelamol and phenol in phenol-melt

| temperature [° C.] | Time [min] | yield % | 3/1 | 2/1 | 1/1 | Dimers/Trimers |
|---|---|---|---|---|---|---|
| 60 | 80 | 47 | 3 | 49 | 18 | 30 |
| 70 | 80 | 63 | 13 | 46 | 3 | 39 |
| 85 | 150 | 73 | 40 | 33 | 0 | 26 |
| 100 | 30 | 65 | 17 | 62 | 2 | 20 |

Example 3

Mannich-Reaction in Phenol Melt in the Presence of Zeolithes 0.5 g (1.9 mmole) Trimelamol are provided in a 50 ml pear shaped flask. 1.66 g (19 mmole) Phenol is added as a crystalline solid. The content of the flask is heated up to 45° until all educts are dissolved in the liquid phenol. Subsequently, molecular sieves (Merck, product no 5705) having pore sizes of 3 Å, 5 Å and 10 Å are added. During the reaction the solution stays clear and transparent.

The reaction melt is mixed with 50 ml chloroform. The organic phase is extracted three times with 50 ml 1.5% NaOH and water. After evaporation of the organic phase a white product was obtained.

Table 3 shows the experimental results in respect to yield, pore size of the zeolithe and product distribution.

TABLE 3

Experimental results of co-condensation of trimelamol and phenol in phenol melt and in the presence of zeolithes

| Temperature [° C.] | Time [min] | yield % | Pore size | mass % | 3/1 | 2/1 | 1/1 | Dimers/Trimers |
|---|---|---|---|---|---|---|---|---|
| 40 | 960 | 80 | 10A | 12 | 34 | 34 | 0 | 33 |
| 60 | 80 | 77 | 10A | 60 | 21 | 56 | 1 | 23 |
| 60 | 80 | 51 | 3A | 18 | 12 | 50 | 4 | 42 |
| 60 | 80 | 79 | 5A | 19 | 12 | 48 | 3 | 38 |
| 70 | 80 | 61 | 5A | 20 | 19 | 44 | 1 | 36 |
| 85 | 150 | 85 | 10A | 60 | 34 | 31 | 0 | 35 |
| 90 | 80 | 85 | 5A | 50 | 37 | 41 | 0 | 21 |

Example 4

Mannich-Reaction in Phenol Melt in the Presence of Zeolithes and Acid 0.5 g (1.9 mmole) Trimelamol are provided in a 50 ml pear shaped flask. 1.66 g (19 mmole) phenol are added as a crystalline solid. The content of the flask is heated up to 45° until all educts are dissolved in the liquid phenol. 100-200 μl Acid is added and after 5 min a molecular sieve, preferably zeoltihe, is added. During the reaction the solution stays clear and transparent.

The reaction melt is mixed with 50 ml chloroform. The organic phase is extracted three times with 50 ml 1.5% NaOH and water. After evaporation of the organic phase a white product was obtained.

Table 4 shows the experimental results in respect to yield, pore size of the zeolithe, acid and product distribution.

TABLE 4

Experimental results of co-condensation of trimelamol and phenol in phenol melt in the presence of zeolithes and acid

| Temperature [° C.] | Time [min] | Yield [%] | Pore size of zeolithe [mass %] | acid | 3/1 | 2/1 | 1/1 | Dimers/Trimers |
|---|---|---|---|---|---|---|---|---|
| 45 | 960 | 79 | 5A 10% | Formic acid | 51 | 30 | 3 | 16 |
| 50 | 180 | 76 | 5A 10% | Formic acid | 36 | 36 | 2 | 22 |
| 60 | 80 | 82 | 5A 15% | Acetic acid | 36 | 41 | 4 | 18 |
| 70 | 80 | 56 | 5A 15% | Formic acid | 53 | 20 | 2 | 26 |
| 70 | 80 | 80 | 5A 20% | Acetic acid | 54 | 24 | 3 | 20 |
| 90 | 80 | 80 | 10A 10% | Formic acid | 53 | 26 | 2 | 18 |

Example 5

Mannich-Reaction in Solvent with Acid as Catalyst 0.5 g (1.9 mmole) Trimelamol are provided 20 ml solvent in a 50 ml pear shaped flask. 2-Cresol is added. The content of the flask is heated up to 50° until all educts are dissolved. Acid is added. During the reaction the solution stays clear and transparent.

The reaction mixture is mixed with 50 ml chloroform. The organic phase is extracted three times with 50 ml 1.5% NaOH and water. After evaporation of the organic phase a white product was obtained.

The obtained yield of the mannich-product differs in dependency of the used solvent, acid catalyst and pH-value (see Table). The highest yield was achieved in chloroform as solvent, and formic acid as catalyst.

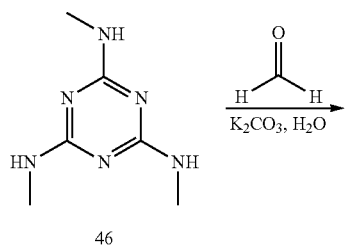

46

-continued

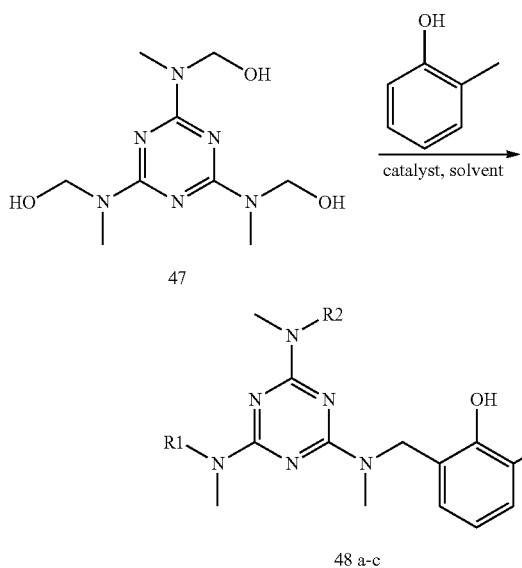

47

→ catalyst, solvent 48 a-c

With 48a

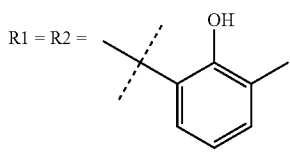

R1 = R2 =

48b:

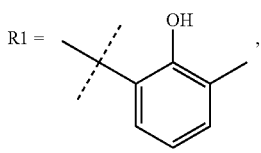

R1 =      , R2=H and

48c: R1=R2=H

Table 5 shows the experimental results in respect to product yield and product distribution.

TABLE 5

Experimental results of co-condensation of trimelamol and cresol using different acid catalysts and solvents

| Entry | molar excess 2-cresol | Catalyst | catalyst molar excess | solvent | reaction time hours | yield %[1] | Found Products |
|---|---|---|---|---|---|---|---|
| 1 | 1.95 | PTSA[2] | 1.1 | CHCl$_3$ | 14 | 44.6 | 46, 48a-c |
| 2 | 1.95 | PTSA[2] | 1.5 | CHCl$_3$ | 14 | 33.6 | 46, 48a-c |
| 3 | 1.96 | acetic acid[3] | — | acetic acid[3] | 18 | 66.5 | 46, 48a-c |
| 4 | 2.46 | HCOOH | 1.5 | CHCl$_3$ | 16.75 | 68.5 | 46, 48a-c |
| 5 | 1.11 | HCOOH | 2.8 | THF | 15 | — | Condensation |
| 6 | 14.6 | HCOOH | 2.9 | 2-cresol | 86 | 16.3[4] | 46, 48a-c |
| 7 | 1.95 | MCIAA[5] | 1.4 | CHCl$_3$ | 18 | 57.0 | 46, 48a-c |

TABLE 5-continued

Experimental results of co-condensation of trimelamol and cresol using different acid catalysts and solvents

| Entry | molar excess 2-cresol | Catalyst | catalyst molar excess | solvent | reaction time hours | yield %[1] | Found Products |
|---|---|---|---|---|---|---|---|
| 8 | 1.99 | TFAA | 3.0 | CHCl$_3$ | 6 | 42.7 | 46, 48a-c |
| 9 | 1.97 | H$_2$SO$_4$ | 1.5 | CHCl$_3$ | 20 | 35.4 | 46, 48a-c |

[1]percent of theoretical amount calculated on 1
[2]4-toluenesulfonic acid,
[3]glacial acetic acid,
[4]after two isolation cycles,
[5]monochloroacetic acid.

Example 6

Mannich-Reaction in Phenol Melt, Acid and Molecular Sieve Followed by Addition of a Formaldehyde Resin 5 g (19 mmole) Trimelamol are provided in a 500 ml flask. 16.6 g (190 mmole) phenol are added as a crystalline solid. The content of the flask is heated up to 45° until all educts are dissolved in the liquid phenol. 2 ml acetic acid is added and after 5 min 1 g molecular sieve 5A is added. The mixture was heated up to 70° C. and stirred for 90 min.

The reaction melt is cooled to 40° C. and mixed with 500 ml chloroform. The organic phase is extracted three times with 500 ml 1.5% NaOH and water. After evaporation of the organic phase a white product is obtained with 51% trisubstituted trimethylmelamine derivative, 28% disubstituted, 5% monosubstituted and 16% dimer products, measured by HPLC.

Urea-formaldehyde glue (66% solid content) is first diluted with water to achieve end solid content 50%. Further on, 3 mass-% of the above product, 2.5 mass-% of a hydrophobic agent are added and homogenised. Finally, 1.5 mass-% of ammonium nitrate is added. The gel time of this glue, tested at 100° C., is 5.0 min.

3 kg of wood chips (Werzalit) are mixed in a rotating drum. With the help of a pump injection 600 g of the glue (50% solid content) is sprayed on the wood chips. 1.4 kg of the so prepared wood chips are put in a metal form of 460×440 mm and pressed to a particle board (PB) with 10 mm thickness. Press temperature is 2000° C. and press time 120 sec. From this PB three test pieces with weight app. 110 g are cut. The pieces are tested according to the EN 120 the so called Perforator method. The formaldehyde content of the three samples is shown in Table 6.

The particle boards (PB) containing the mannich compounds according to the invention fulfil the emission limit of the standard requirements of F**** resp. Super E-zero (standard for formaldehyde emission levels of PB).

Comparative example 6 without the Mannich compounds according to the invention: Urea-formaldehyde glue (66% solid content) is diluted with water to 50% end solid content. Furtheron 2.5 mass-% Hydrophobic agent is added and the mixture is homogenised. As last 1.5 mass-% ammonium nitrate is added. The gel time of this glue, tested at 100° C. is 4.8 min. With this glue wood chips are prepared and a particle board is pressed under the same conditions of Example 6. The formaldehyde content of these particle boards was also determined under the above conditions and the results are shown in Table 6.

Table 6 shows the formaldehyde content in particle boards containing the Mannich compounds according to the invention (Example 6, piece 1-3) and without these compounds (comparative example 6, piece 1-3). It is evident that the boards comprising the Mannich compounds are characterized by strongly reduced formaldehyde content and thus showing the formaldehyde scavenging property of the Mannich compounds according to the invention in the wood-working industry.

TABLE 6

Formaldehyde content in different particle boards tested according to EN120

| Test pieces | Formaldehyde content (mg/100 g PB) |
|---|---|
| Example 6, piece 1 | 1.5 |
| Example 6, piece 2 | 1.2 |
| Example 6, piece 3 | 1.3 |
| Comparative example 6, piece 1 | 13.8 |
| Comparative example 6, piece 2 | 14.6 |
| Comparative example 6, piece 3 | 12.3 |

Example 7

Mannich-Reaction in Formalin Solution and Formic Acid as Catalyst

In a 500 cm³ three-necked round bottom flask equipped with a thermometer 25.05 g (0.0970 mol) $N^2,N^4,N^6$-tris[(trihydroxymethyl)trimethylamino]-1,3,5-triazine and 100.10 g (1.06 mol) phenol were solved in 25.5 cm³ (0.322 mol) formalin solution (35%). The flask was temperated to 15° C. and 140.0 cm³ (3.64 mol) formic acid were added rapidly. The temperature rise to ~26° C. and the clear reaction mixture is stirred at ambient temperature for four hours followed by stirring at 50° C. for one hour. The crude reaction mixture contains 85.2% Mannich base 30 (see below).

250 cm³ Deionised water were added to the crude reaction mixture, heated to boiling point for a few minutes and cooled rapidly to room temperature. A high viscous residue separates, the overlaying aqueous phase is decanted and the residue washed with water once. Repeating the washing-process eight times afford the crude reaction product. After the last washing procedure the high viscous (nearly solid) residue is solved in acetone which is further evaporated at reduced pressure (50° C. bath temperature) yielding the crude reaction product in 76.8% as a white solid with a melting point between 81 and 86° C.

The chemical composition of the crude reaction product mixture was determined by LC-MS/UV-VIS detection applying the following conditions:

HPLC: THERMO ELECTRON CORPORATION FINIGAN SURVEYOR MS Pump Plus, Autosampler Plus, PDA Plus Detector
solvent A: 0.1% formic acid in water (pH=2.47)
solvent B: acetonitrile
column: Zorbax SB-C18, 2.1×150 mm, 5 micro
column temperature: 40° C.
flow: 200 mm³·min$^{-1}$
injection volume: 10 mm³
UV detection: 254 nm
sample preparation: ~0.15 mg·cm$^{-3}$ in acetonitrile:water=60:40

| | t/min | solv. A | solv. B |
|---|---|---|---|
| gradient program: | 0 | 70 | 30 |
| | 10 | 70 | 30 |
| | 40 | 0 | 100 |
| | 45 | 0 | 100 |
| | 45.1 | 70 | 30 |
| | 50 | 70 | 30 |

MS: ESI
ms² datadependent scan
m/z=80-1000
fragmentation energy=35%

The reaction mixture has the following composition calculated via peak areas from the LC-MS/UV-VIS detection: 21 (76.8%), 26 (13.0%), 49 (7.0%) and 21-CH₂OH (3.5%).

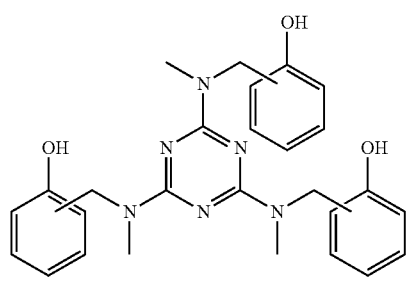

21

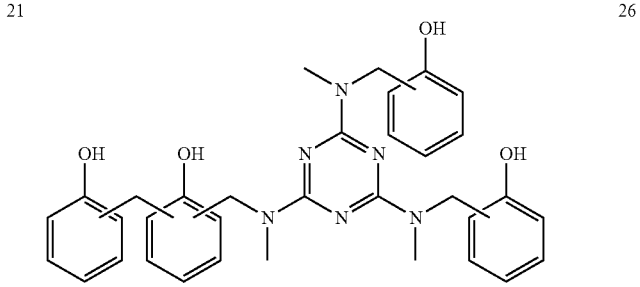

26

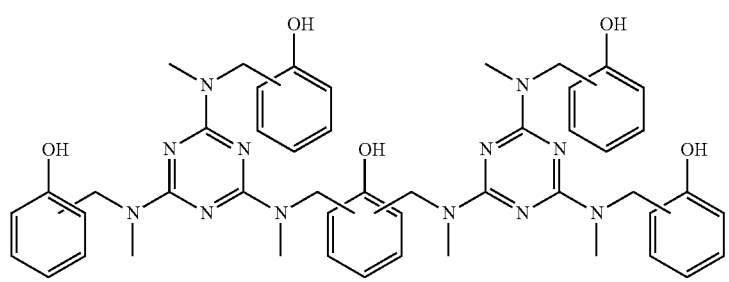

49

Figure 2:
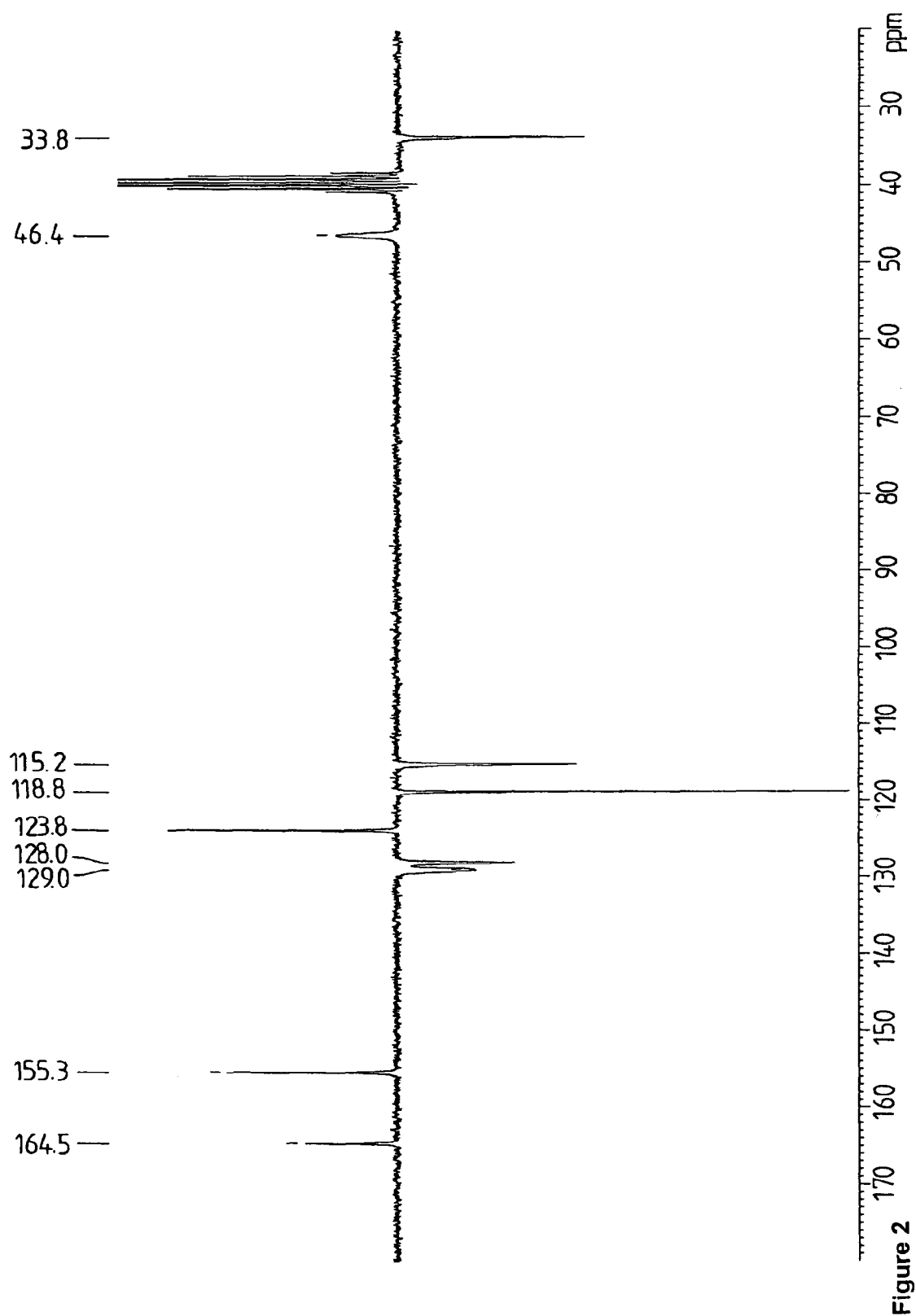
FIG. 2 a $^{13}$C-NMR spectra of a compound according to the invention

The crude reaction product mixture was further purified by chromatography on silica gel (mobile phase:chloroform) providing the (ooo)-isomer of Mannich base 21 as a white solid with a melting point of 199-200° C. FIG. 1 shows a $^1$H-NMR spectra of (ooo)-21 taken in DMSO-d6 at 200 MHz and 30° C. FIG. 2 shows a $^{13}$C-NMR of (ooo)-21 taken in DMSO-d6 at 50 MHz and 30° C. and using a APT pulse program.

Figure 3:
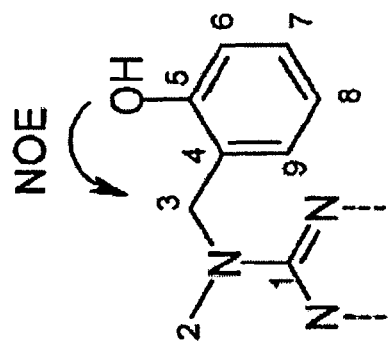
FIG. 3 a scheme showing the atom numbering for a compound according to the invention

FIG. 3 shows the chosen atom numbering for (ooo)-21 used in the full characterization via $^1$H-NMR (see FIG. 1), $^{13}$C-NMR (see FIG. 2) and 2D-NMR experiments. The signals are assigned to: 9.60 (—OH), 6.76 ($H^8$), 6.80 ($H^6$), 7.05 ($H^9$), 7.08 ($H^7$), 4.70 (—$CH_2$—), 3.03 (—$CH_3$) ppm (FIG. 2) and 164.5 ($C^1$), 155.3 ($C^8$), 129.0 ($C^9$), 128.0 ($C^7$), 123.8 ($C^4$), 118.8 ($C^8$), 115.2 ($C^6$), 46.4 ($C^3$) and 33.8 ($C^2$) ppm (FIG. 3). The nuclear Overhauser exchange (NOE) correlation peaks (4.70⇌9.88, 9.82, 9.58 ppm) proved the (ooo)-structure.

Additionally, ultimate analysis of the isolated (ooo)-21 isomer showed good accordance to the calculated values: molecular composition=C: 65.51% (cal. 66.65%), H: 6.28% (cal. 6.21%) and N: 16.83% (cal. 17.27%). Correcting the values with 1.52% water content, calculated from excess oxygen, obtained: C: 65.52%, H: 6.19% and N: 17.09%.

Example 8

Mannich-Reaction in Formalin Solution and Formic Acid as Catalyst

In a 500 cm$^3$ three-necked round bottom flask equipped with a thermometer 18.2 g (0.1 mol) $N^2,N^2,N^4,N^6$-tetra[(dihydroxymethyl)tetramethylamino]-1,3,5-triazine (Tetramelamol) and 70.5 g (0.75 mol) phenol were solved in 17.1 g (0.2 mol) formalin solution (35%). The flask was temperated to 15° C. and 112 g (3.6 mol) formic acid were added rapidly. The temperature rise to ~20° C. and the clear reaction mixture is stirred at ambient temperature for 5 hours. The crude reaction mixture contains 91% Mannich base of the following structure:

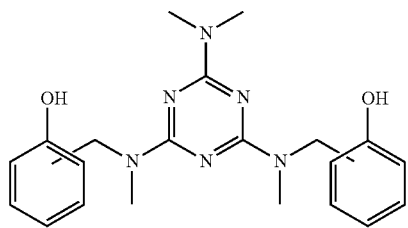

51

250 cm$^3$ deionised water were added to the crude reaction mixture, heated to boiling point for a few minutes and cooled rapidly to room temperature. A high viscous residue separates, the overlaying aqueous phase is decanted and the residue washed with water once. Repeating the washing-process twice afford the crude reaction product. After the last washing procedure the high viscous (nearly solid) residue is solved in acetone which is further evaporated at reduced pressure (50° C. bath temperature) yielding the crude reaction product in 85% as a white solid.

Chemical composition of the crude reaction product mixture was 33 (91%), oligomers mixture (9%) calculated via peak areas from the LC-MS/UV-VIS detection.

Example 9

Mannich-Reaction in Formalin Solution and HCl as Catalyst

In a 500 cm$^3$ three-necked round bottom flask equipped with a thermometer 16.8 g (0.1 mol) $N^2,N^4,N^6$-tris[(trihydroxymethyl)trimethylamino]-1,3,5-triazine and 94 g (1 mol) phenol were solved in 200 ml Dioxan and 25.7 g (0.3 mol) formalin solution (35%). The flask was temperated to 15° C. and 10.6 g (0.3 mol) hydrochloric acid were added rapidly. The temperature rise to ~28° C. and the clear reaction mixture is stirred at ambient temperature for 3 hours. The crude reaction mixture contains 95.9% Mannich base mixture.

250 cm$^3$ deionised water were added to the crude reaction mixture, heated to boiling point for a few minutes and cooled rapidly to room temperature. A high viscous residue separates, the overlaying aqueous phase is decanted and the residue washed with water once. Repeating the washing-process 5 times afford the crude reaction product. After the last washing procedure the high viscous (nearly solid) residue is solved in acetone which is further evaporated at reduced pressure (50° C. bath temperature) yielding the crude reaction product in 88% as a white solid.

Chemical composition of the crude reaction product mixture was 19 (6.8%), 20 (65.9%), 21 (22.3%), 4.1% trimelamol and oligomers (0.9%) as calculated via peak areas from the LC-MS/UV-VIS detection.

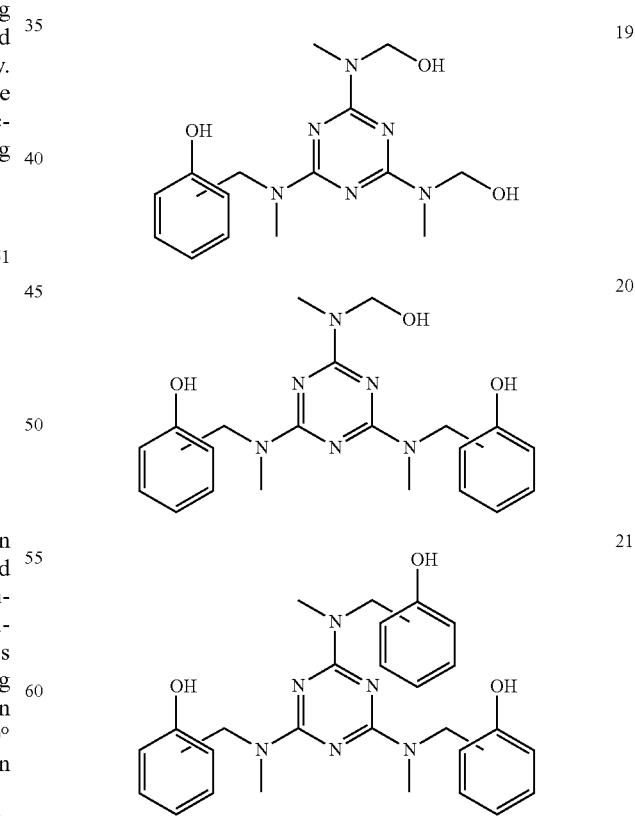

Example 10

Synthesis of Trimethylmelamin-Phenol-Mannich Bases (21, $C_{27}H_{30}N_6O_3$)

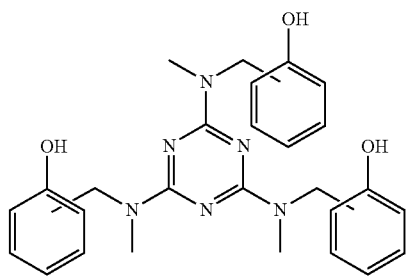

In a 500 cm³ three-necked round bottom flask, equipped with a thermometer and a condenser, 25.05 g (0.0970 mol) 2,4,6-tris[(trihydroxymethyl)trimethylamino]-1,3,5-triazine and 100.10 g (1.06 mol) phenol are dissolved in 25.5 cm³ (0.322 mol) aqueous formaldehyde solution (35%). The flask is tempered to 15° C. and 140.0 cm³ (3.64 mol) formic acid are added rapidly. The temperature rises to about 26° C. and the clear reaction mixture is stirred at ambient temperature for four hours followed by stirring at 50° C. for one hour. The crude reaction mixture contains 85.2% Mannich base 21. 250 cm³ Deionized water were added to the crude reaction mixture, heated to boiling point for a few minutes, and cooled rapidly to room temperature. A high viscous residue separates, the overlaying aqueous phase is decanted, and the residue washed with water once. Repeating the washing-process eight times affords the crude reaction product. After the last washing procedure the highly viscous (nearly solid) residue is dissolved in acetone and evaporation of the solvent under reduced pressure (50° C. bath temperature) yields the crude reaction product, containing 76.8% 21, as a white solid (mp: 81-86° C.). Chemical composition of the crude reaction product: 21 (76.8%), 24 (1.75%), 26 (13.0%), 49 (7.0%). Calculated from LC-MS (UV detection trace) peak areas without response factor correction.

Characterization of 2,2',2"-(1,3,5-Triazine-2,4,6-triyl)tris(methylazanediyl)-tris(methylene) triphenol ((o,o,o)-21, 34):

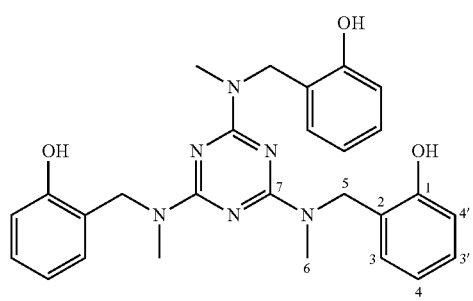 [SMILES: CN(Cc1ccccc1O)c1nc(N(C)Cc2ccccc2O)nc(N(C)Cc2ccccc2O)n1]

Mp: 199-200° C., ¹H NMR (200 MHz, DMSO-d6, 30° C.): δ=9.60 (s, 1H, 1-OH), 6.80-7.10 (m, 2H, H3 and H3'), 6.71-6.81 (m, 2H, H4 and H4'), 4.70 (s, 2H, H5), 3.03 (s, 3H, H6) ppm ¹³C NMR (50 MHz, DMSO-d6, 30° C.): δ=164.5 (C7), 155.3 (C1), 129.0 (C3), 128.0 (C3'), 123.8 (C2), 118.8 (C4), 115.2 (C4'), 46.40 (C5), 33.80 (C6) ppm Ultimate analysis: C, 65.51% (cal. 66.65%); H, 6.28% (cal. 6.21%); N, 16.83% (cal. 17.27%). Corrected values for 1.52% water content calculated from excess oxygen: C, 65.52%; H, 6.19%; N, 17.09%.

Example 11

Synthesis of Tetramethylmelamin-Phenol-Mannich Base (51, $C_{21}H_{26}N_6O_2$)

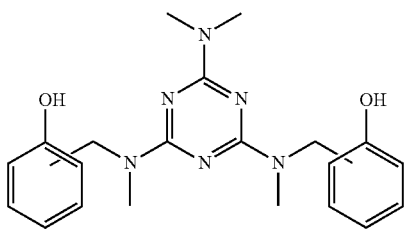

In a 50 cm³ round bottom flask 0.990 g (4.09 mmol) 2,4-bis[(hydroxymethyl)methylamino]-6-dimethylamino-1,3,5-triazine and 3.030 g (32.2 mmol) phenol are dissolved in 650 mm³ (8.22 mmol) aqueous formaldehyde solution (35%). 5.6 cm³ Formic acid (98%) are added and the reaction mixture is stirred at room temperature for five hours, followed by stirring at 50° C. for one hour. 25 cm³ Deionized water are then added to the crude reaction mixture, heated to boiling point for a few minutes and cooled rapidly to room temperature. A high viscous residue separates, the overlaying aqueous phase is decanted, and the residue washed with water once. Repeating the washing-process three times yields the crude reaction product. After the last washing procedure the highly viscous (nearly solid) residue is dissolved in acetone and evaporation of the solvent under reduced pressure (50° C. bath temperature) yields 1.53 g crude reaction product as a white solid containing 91% Mannich base 51 (calculated from LC-MS peak areas without response factor correction).

Isolation of the isomers: the constitutional isomers were separated from the crude reaction product (1.998 g) with column chromatography on Silica Gel 60, using toluene/acetonitrile (10:1) as the mobile phase, yielding 0.75 g (50.9%) (o,o)-51, 52, 0.63 g (42.8%) (o,p)-51, 53, and 0.093 g (6.3%) (p,p)-51, 54.

Characterization of 2,2'-(6-(Dimethylamino)-1,3,5-triazine-2,4-diyl)bis(methylazanediyl)bis(methylene) diphenol ((o,o)-51, 52)

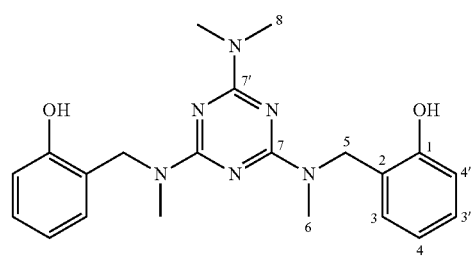 [SMILES: CN(C)c1nc(N(C)Cc2ccccc2O)nc(N(C)Cc2ccccc2O)n1]

Mp: 156-157° C. ¹H NMR (200 MHz, DMSO-d6, 30° C.): δ=9.80 (s, 2H, 1-OH), 7.04-7.11 (m, 2H, H3 and H3'), 6.73-

6.81 (m, 2H, H4 and H4'), 4.69 (s, 2H, H5), 3.05 (s, 3H, H8), 3.02 (s, 3H, H6) ppm $^{13}$C NMR (50 MHz, DMSO-d6, 30° C.): δ=164.6 (C7 and C7'), 155.4 (C1), 129.2 (C3), 128.2 (C3'), 123.9 (C2), 118.8 (C4), 115.4 (C4'), 46.50 (C5), 35.66 (C8), 33.59 (C6) ppm IR (KBr)=3077, 3938, 2707, 2615, 2358, 1586, 1548, 1485, 1444, 1399, 1348, 1319, 1248, 1150, 1100, 1052, 1039, 947, 869, 808, 753 cm$^{-1}$ ESI-MS (AcN:H$_2$O=4:1, c~0.1 mg·cm$^{-3}$, positive ion mode): m/z=395.3 [51+H]$^+$ Characterization of 2,4'-(6-(Dimethylamino)-1,3,5-triazine-2,4-diyl)bis(methylazanediyl)bis(methylene)diphenol ((o,p)-51, 53)

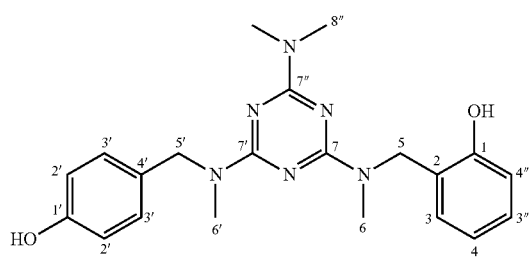 [SMILES: CN(C)c1nc(N(C)Cc2ccc(O)cc2)nc(N(C)Cc2ccccc2O)n1]

Mp: 80-81° C. $^1$H NMR (200 MHz, DMSO-d6, 30° C.): δ=9.89 (s, 1H, 1-OH), 9.23 (s, 1H, 1'-OH), 7.05-7.19 (m, 4H, H3, H3', and H3"), 6.5-6.81 (m, 4H, H2', H4, and H4'), 4.68 (s, 2H, H5), 4.64 (s, 2H, H5'), 3.05 (s, 6H, H8 and H8'), 3.02 (s, 3H, H6'), 3.95 (s, 3H, H6) ppm $^{13}$C NMR (50 MHz, DMSO-d6, 30° C.): δ=164.7 (C7"), 164.5 (C7 and C7'), 156.3 (C1'), 155.4 (C1), 129.3 (C3), 128.9 (C3'), 128.7 (C4'), 128.2 (C3"), 123.9 (C2), 118.8 (C4), 115.4 (C4'), 115.0 (C2'), 50.14 (C5'), 46.57 (C5), 35.58 (C8 and C8'), 33.52 (C6), 33.22 (C6') ppm IR (KBr)=3383, 2931, 2703, 2610, 2359, 2342, 1586, 1542, 1445, 1398, 1351, 1320, 1247, 1169, 1101, 1052, 866, 807, 755 cm$^{-1}$ ESI-MS (AcN:H$_2$O=4:1, c~0.1 mg·cm$^{-3}$, positive ion mode): m/z=395.3 [51+H]$^+$ Characterization of 2,2'-(6-Dimethylamino)-1,3,5-triazine-2,4-diyl)bis(methylazanediyl)bis(methylene)diphenol ((p,p)-51, 54)

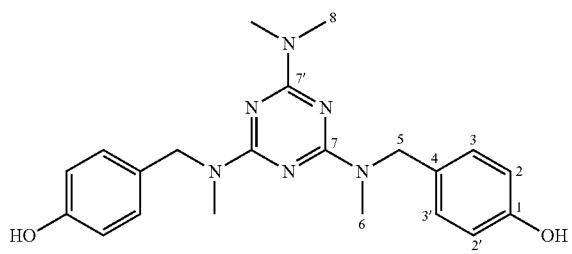

Mp: paste-like at ambient temperature. $^1$H NMR (200 MHz, DMSO-d6, 30° C.): δ=9.23 (s, 1H, 1-OH), 7.06 (d, J=7.43 Hz, 2H, H3 and H3'), 6.68 (d, J=7.43 Hz, 2H, H2 and H2'), 4.64 (s, 2H, H5), 3.05 (s, 3H, H8), 2.95 (s, 3H, H6) ppm $^{13}$C NMR (50 MHz, DMSO-d6, 30° C.): δ=165.3 (C7'), 165.0 (C7), 156.3 (C1), 128.9 (C4), 128.8 (C3 C3'), 115.0 (C2 and C2'), 50.00 (C5), 33.17 (C6), 35.47 (C8) ppm ESI-MS (AcN:H$_2$O=4:1, c~0.1 mg·cm$^{-3}$, positive ion mode): m/z=395.3 [51+H]$^+$ Example 12

Synthesis of Pentamethylmelamin-Phenol-Mannich Bases (50, $C_{15}H_{22}N_6O$)

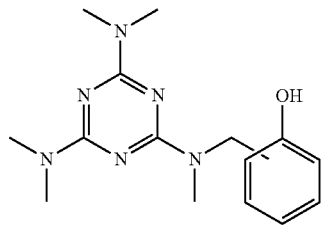

In a 25 cm$^3$ round bottom flask 0.50 g (2.21 mmol) 2-[(hydroxymethyl)methylamino]-4,6-bis(dimethylamino)-1,3,5-triazine and 1.28 g (13.6 mmol) phenol are dissolved in 175 mm$^3$ (2.21 mmol) aqueous formaldehyde solution (35%). 1.4 cm$^3$ Formic acid (98%) are added and the reaction mixture is stirred at room temperature for five hours, followed by stirring at 50° C. for one hour. 10 cm$^3$ Deionized water are added to the crude reaction mixture, heated to boiling point for a few minutes, and cooled rapidly to room temperature. A highly viscous residue separates, the overlaying aqueous phase is decanted, and the residue washed with water once. Repeating the washing process three times affords the crude reaction product. After the last washing procedure the highly viscous (nearly solid) residue is dissolved in acetone and evaporation of the solvent under reduced pressure (50° C. bath temperature) yields the crude reaction product as a white solid containing 74.5% Mannich base 50 (calculated as peak areas from LC-MS).

Characterization of 2-(((4,6-Bis(dimethylamino)-1,3,5-triazine-2-yl)(methyl)-amino)methyl) phenol ((o)-50, 55)

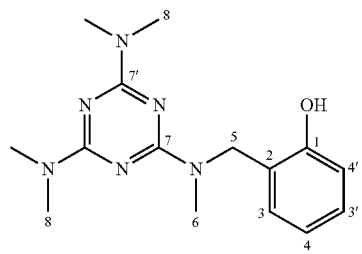 [SMILES: CN(C)c1nc(N(C)C)nc(N(C)Cc2ccccc2O)n1]

Mp: 169-171° C. $^1$H NMR (200 MHz, DMSO-d6, 30° C.): δ=9.91 (s, 1H, 1-OH), 7.05-7.12 (m, 2H, H3 and H3'), 6.70-6.80 (m, 2H, H4 and H4'), 4.66 (s, 2H, H5), 3.04 (s, 12H, H8), 3.02 (s, 3H, H6) ppm 13C NMR (50 MHz, DMSO-d6, 30° C.): δ=164.8 (C7'), 164.6 (C7), 155.5 (C1), 129.5 (C3), 128.3 (C3'), 123.9 (C2), 118.7 (C4), 115.5 (C4'), 46.59 (C5), 35.53

(C8), 33.35 (C6) ppm ESI-MS (AcN:H$_2$O=4:1, c~0.1 mg·cm$^{-3}$, positive ion mode): m/z=303.3 [50+H]$^+$ Characterization of 4-(((4,6-Bis(dimethylamino)-1,3,5-triazine-2-yl)(methyl)amino)-methyl) phenol ((p)-50, 56)

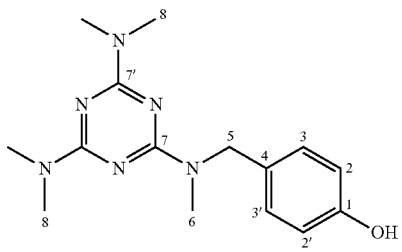

Mp: 163-164° C. $^1$H NMR (200 MHz, DMSO-d6, 30° C.): δ=9.22 (s, 1H, 1-OH), 7.07 (d, J=8.48 Hz, 2H, H3 and H3'), 6.69 (d, J=4.48 Hz, 2H, H2 and H2'), 4.64 (s, 2H, H5), 3.03 (s, 12H, H8), 2.94 (s, 3H, H6) ppm $^{13}$C NMR (50 MHz, DMSO-d6, 30° C.): δ=165.2 (C7'), 165.0 (C7), 156.3 (C1), 129.0 (C4), 128.8 (C3 and C3'), 115.0 (C2 and C2'), 50.0 (C5), 33.10 (C6), 35.4 (C8) ppm IR (KBr): 2933, 2868, 2790, 1736, 1614, 1540, 1444, 1394, 1359, 1316, 1263, 1217, 1168, 1149, 1103, 1054, 982, 950, 866, 848, 806, 622, 570, 534, 504 cm$^{-1}$ ESI-MS (AcN:H$_2$O=4:1, c~0.1 mg·cm$^{-3}$, positive ion mode): m/z=303.3 [50+H]$^+$ Example 13

Synthesis of 4,4',4"-(1,3,5-Triazine-2,4,6-triyl)tris(methylazanediyl)tris(methylene)tris(2,6-dimethylphenol) (57, C$_{33}$H$_{42}$N$_6$O$_3$)

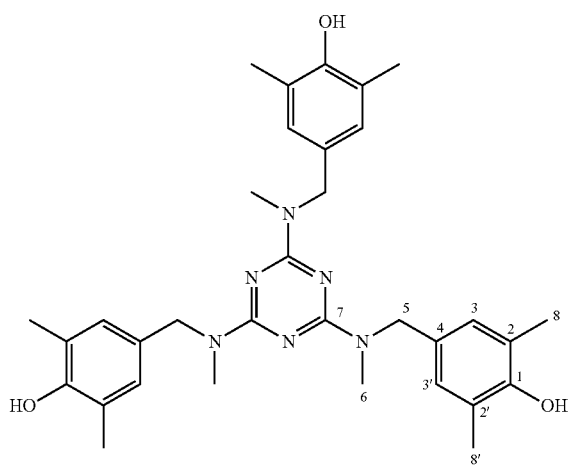

In a 25 cm$^3$ round bottom flask 0.507 g (1.936 mmol) 2,4,6-tris[(trihydroxymethyl)methylamino]-1,3,5-triazine and 1.449 g (11.86 mol) 2,6-dimethylphenol are dispersed in 460 mm$^3$ (5.817 mmol) aqueous formaldehyde solution (35%). 2.8 cm$^3$ (74.2 mmol) Formic acid are added and the clear reaction mixture is stirred at ambient temperature for three hours, followed by stirring at 50° C. for one hour. 15 cm$^3$ Deionized water are added to the crude reaction mixture, heated to boiling point for a few minutes and cooled rapidly to room temperature. A high viscous residue separates, the overlaying aqueous phase is decanted, and the residue washed with water once. Repeating the washing process four times affords the crude reaction product. After the last washing procedure the highly viscous (nearly solid) residue is dissolved in acetone and evaporation of the solvent under reduced pressure (50° C. bath temperature) yields the crude reaction product as a colourless solid containing 92.5% 57 (87.5% conversion).

Mp: 176-180° C. $^1$H NMR (200 MHz, DMSO-d6, 30° C.): δ=8.03 (s, 1H, 1-OH), 6.80 (s, 2H, H3 and H3'), 4.61 (s, 2H, H5), 2.95 (s, 3H, H6), 2.09 (s, 6H, H8 and H8') ppm $^{13}$C NMR (50 MHz, DMSO-d6, 30° C.): δ=165.1 (C7), 152.1 (C1), 129.0 (C4), 127.6 (C3 and C3'), 123.9 (C2 and C2'), 50.12 (C5), 33.20 (C6), 16.58 (C8) ppm ESI-MS (AcN:H$_2$O=4:1, c~0.1 mg·cm$^{-3}$, positive ion mode): m/z=571.6 [57+H]$^+$ Example 14

LC-MS Methods for the Analysis of Mannich Bases

Method for Mannich Bases from 2-Cresol as CH-Acidic Component solvent A: 0.1% formic acid in water (pH=2.47)
solvent B: acetonitrile
column: Zorbax SB-C18, 250×4.6 mm, 5 μm
column temperature: 40° C.
flow: 1000 mm$^3$·min$^{-1}$
injection volume: 50 mm$^3$
UV detection: 254 nm
sample preparation: ~0.15 mg·cm$^{-3}$ in acetonitrile:water=1:1

|  | t/min | solv. A | solv. B |
|---|---|---|---|
| gradient program: | 0 | 50 | 50 |
|  | 30 | 0 | 100 |
|  | 35 | 0 | 100 |
|  | 35.1 | 50 | 50 |
|  | 45 | 50 | 50 |

MS: ESI
ms$^2$ datadependent scan
m/z=80-1000
fragmentation energy=35%

Method for Mannich Bases from Phenol as CH-Acidic Component solvent A: 0.1% formic acid in water (pH=2.47)
solvent B: acetonitrile
column: Zorbax SB-C18, 2.1×150 mm, 5 μm
column temperature: 40° C.
flow: 200 mm$^3$·min$^{-1}$
injection volume: 10 mm$^3$
UV detection: 254 nm

|  | t/min | solv. A | solv. B |
|---|---|---|---|
| gradient program: | 0 | 70 | 30 |
|  | 10 | 70 | 30 |
|  | 40 | 0 | 100 |
|  | 45 | 0 | 100 |
|  | 45.1 | 70 | 30 |
|  | 50 | 70 | 30 |

-continued

| | t/min | solv. A | solv. B |
|---|---|---|---|
| gradient program for bifunctional Mannich base 25 | 0 | 80 | 20 |
| | 10 | 70 | 30 |
| | 45 | 0 | 100 |
| | 50 | 0 | 100 |
| | 50.1 | 80 | 20 |
| | 55 | 80 | 20 | sample preparation: ~0.15 mg·cm$^{-3}$ in acetonitrile:water=3:2

MS: ESI ms$^2$ datadependent scan m/z=80-1000 fragmentation energy=35%

The invention claimed is:

1. A melamine-based Mannich compound selected from the group consisting of the following formulae (7) to (11):

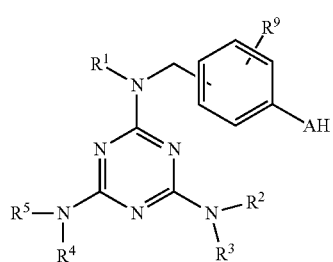

7

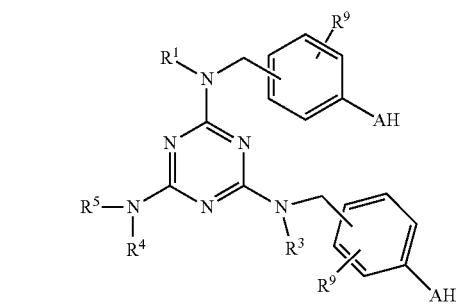

8

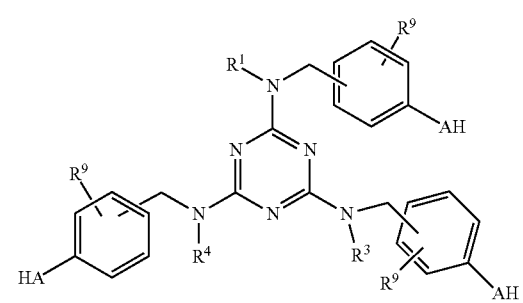

9

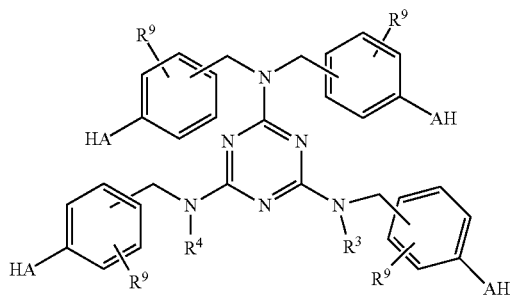

10

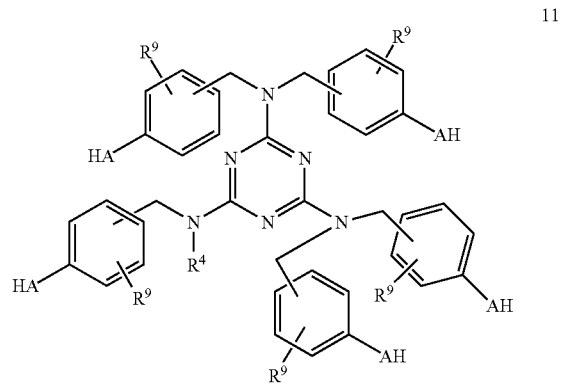

11 wherein

A is O, the moieties R$^1$, R$^2$ and R$^5$ are selected from a group comprising H, non-substituted C$_1$-C$_{50}$-alkyl, non-substituted C$_2$-C$_{50}$-alkenyl, non-substituted C$_2$-C$_{50}$-alkinyl, non-substituted C$_3$-C$_{10}$-cycloalkyl, non-substituted C$_5$-C$_7$-cycloalkenyl, which in each case can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—, the moieties R$^3$ and R$^4$ are selected from a group comprising non-substituted C$_1$-C$_{50}$-alkyl, non-substituted C$_2$-C$_{50}$-alkenyl, non-substituted C$_2$-C$_{50}$-alkinyl, non-substituted C$_3$-C$_{10}$-cycloalkyl, non-substituted C$_5$-C$_7$-cycloalkenyl, which in each case can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—, the moiety R$^9$ is selected from a group comprising H, substituted or non-substituted hydroxy, substituted or non-substituted amino, halogen, substituted or non-substituted C$_1$-C$_{12}$-alkyl, substituted and non-substituted C$_3$-C$_7$-cycloalkyl, substituted and non-substituted C$_2$-C$_{12}$-alkenyl, substituted or non-substituted aryl, whereby the substituted aryl can be bound via at least one methylene bridge to the aromatic structure and can be a group of the formula:

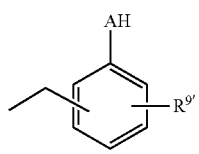

wherein R⁹' has the meaning of R⁹; substituted or non-substituted heteroaryl, substituted and non-substituted carbonyl, substituted and non-substituted $C_1$-$C_{50}$-alkyl, substituted and non-substituted $C_1$-$C_{50}$-alkenyl, substituted and non-substituted $C_1$-$C_{50}$-alkinyl, substituted and non-substituted $C_3$-$C_{10}$-cycloalkyl, substituted and non-substituted $C_5$-$C_7$-cycloalkenyl, whereby each alkyl, alkenyl and alkinyl chain, can be interrupted by one or more oxygen atoms, sulphur atoms, substituted or mono-substituted nitrogen atoms, double bonds, siloxan groups and/or by one or more groups of the type —C(O)O—, —OC(O)—, —C(O)—, —NHC(O)O—, —OC(O)NH— and/or —OC(O)O—, and whereby up to four moieties R⁹ are present on the aromatic ring, and mixtures thereof.

2. The compound according to claim 1, wherein, the moieties $R^1$, $R^2$, $R^3$, $R^4$ and $R^5$ are selected from a group comprising non-substituted $C_1$-$C_{12}$-alkyl, substituted and non-substituted $C_3$-$C_7$-cycloalkyl and substituted and non-substituted $C_2$-$C_{12}$-alkenyl.

3. The compound according to claim 1, wherein, the moiety $R^9$ is selected from a group comprising —OH, —OCH₃, —OC₂H₅, —NH₂, —CH₃, —C₂H₅, substituted and non-substituted $C_6$-$C_{12}$ Aryl, —CH₂C₆H₅, —C(CH₃)₂C₆H₅ or —CH₂C₆H₄AH.

4. The compound according to claim 2, wherein, the moiety $R^9$ is selected from a group comprising —OH, —OCH₃, —OC₂H₅, —NH₂, —CH₃, —C₂H₅, substituted and non-substituted $C_6$-$C_{12}$ Aryl, —CH₂C₆H₅, —C(CH₃)₂C₆H₅ or —CH₂C₆H₄AH.

5. The compound according to claim 1, wherein said compound is selected from the group consisting of the following formulae (13) to (18):

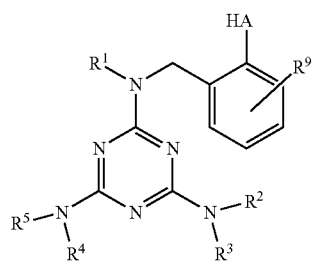

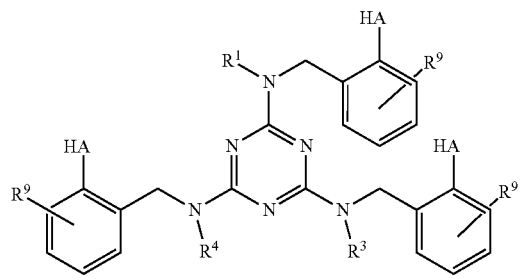

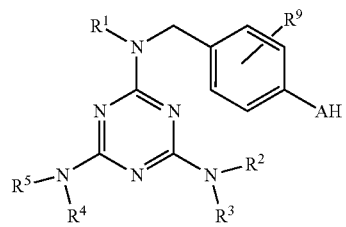

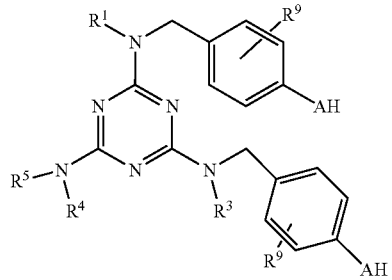

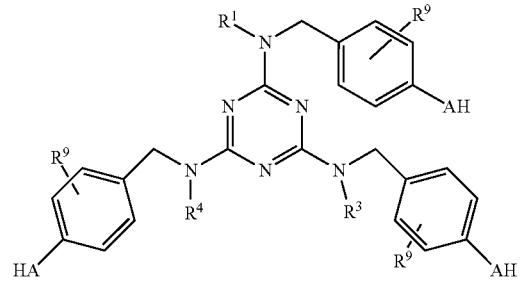

and mixtures thereof, wherein $R^1$, $R^2$, $R^3$, $R^4$, $R^5$, and A have the above meanings.

6. The compound according to claim 1, wherein said compound is selected from the group consisting of the following formulae (19) to (21), (23), (24), (26), (27), and (49) to (51):

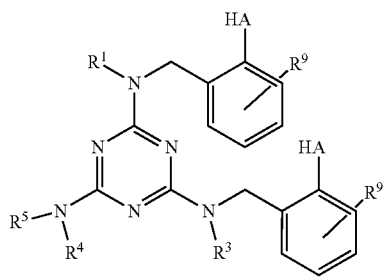

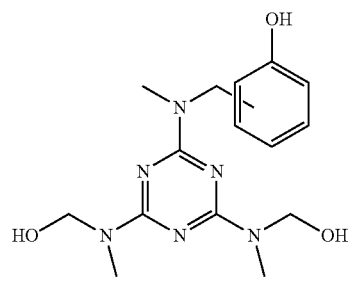

-continued
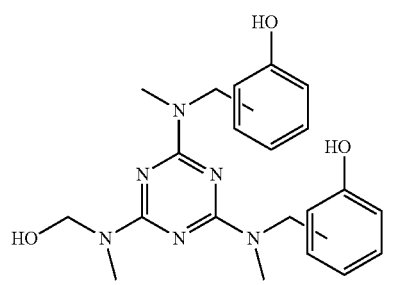
20
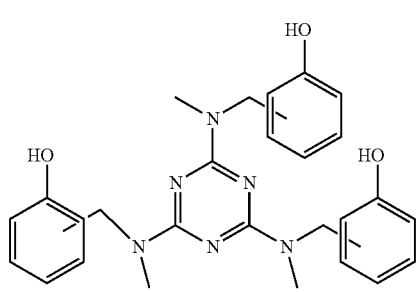
21
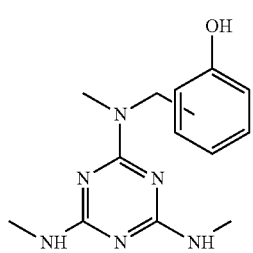
23
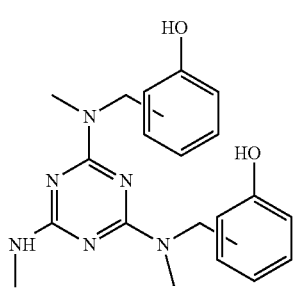
24
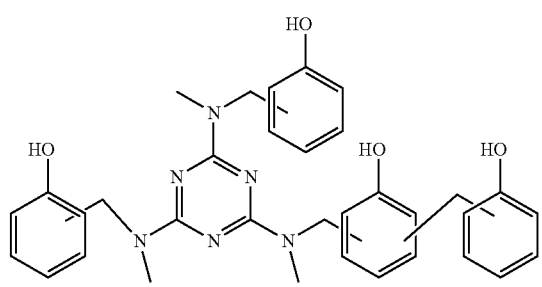
26
-continued
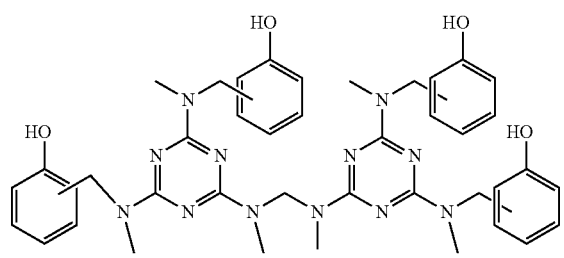
27
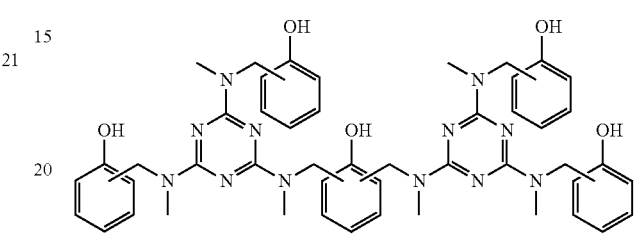
49
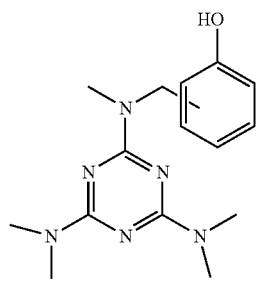
50
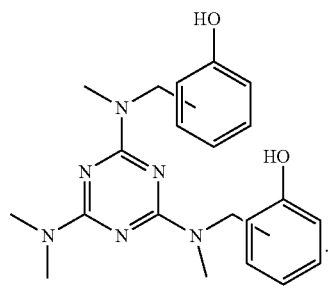
51
7. A process for synthesizing a compound according to claim 1 comprising the steps of:
a) reacting at least one melamine (36) with formaldehyde (37) under basic conditions to form at least one compound (38) according to the reaction scheme I,
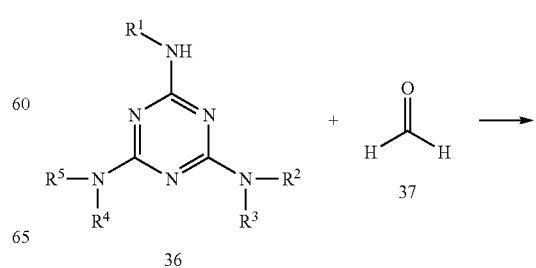

-continued

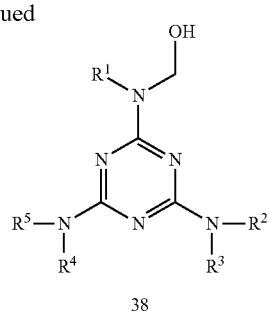

38 b) reacting the at least one compound (38) in the presence of at least one catalyst to form at least one Mannich-base (39) according to the reaction scheme II,

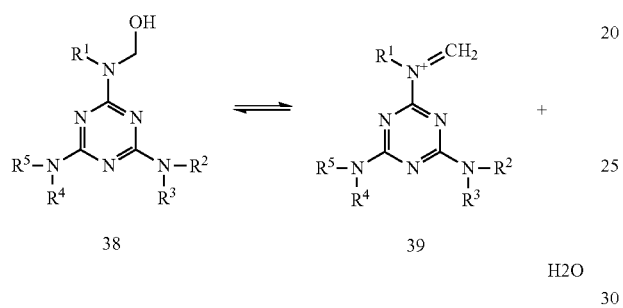

c) reacting the at least one Mannich-base (39) with at least one substituted or non-substituted aromatic compound of the formulae (41) to form at least one of the compounds according to the formulae (7) to (18) according to the reaction scheme IV

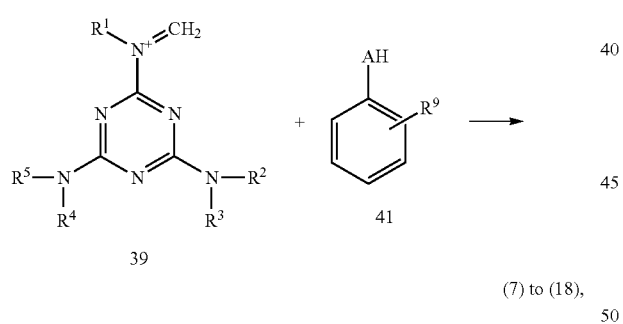

(7) to (18), and
d) working up the reaction mixture,
wherein the moieties $R^1$, $R^2$, $R^3$, $R^4$, $R^5$ and $R^9$ and A have the above meanings.

8. The process according to claim 7, wherein step a) is carried out at a pH between 8 and 12, in the presence of an inorganic or organic base, and steps b) and c) are carried out at a pH between 1-6.

9. The process according to claim 7, wherein the catalyst used in steps b) and c) is selected from a group comprising sulphonic acid, sulphuric acid, trifluoracetic acid (TFAA), 4-toluenesulphonic acid (pTSA), monochloracetic acid (MCAA), glacial acetic acid, formic acid, hydrochloric acid and molecular sieve.

10. The process according to claim 7, wherein steps b) and c) are carried out in a solvent, or in substance.

11. A precondensate comprising the reaction product of components comprising at least one compound according to claim 1 with at least one aldehyde.

12. The precondensate according to claim 11, wherein the at least one aldehyde is formaldehyde, acetaldehyde, furan-2-aldehyde (furfural), glyoxal and/or trans-3-phenyl-2-propenal (cinnamaldehyde).

13. The precondensate according to claim 12, wherein the components further comprise at least one aromatic compound and/or other precondensates.

14. The precondensate according to claim 11, wherein said precondensate is selected from the group consisting of the following structures:

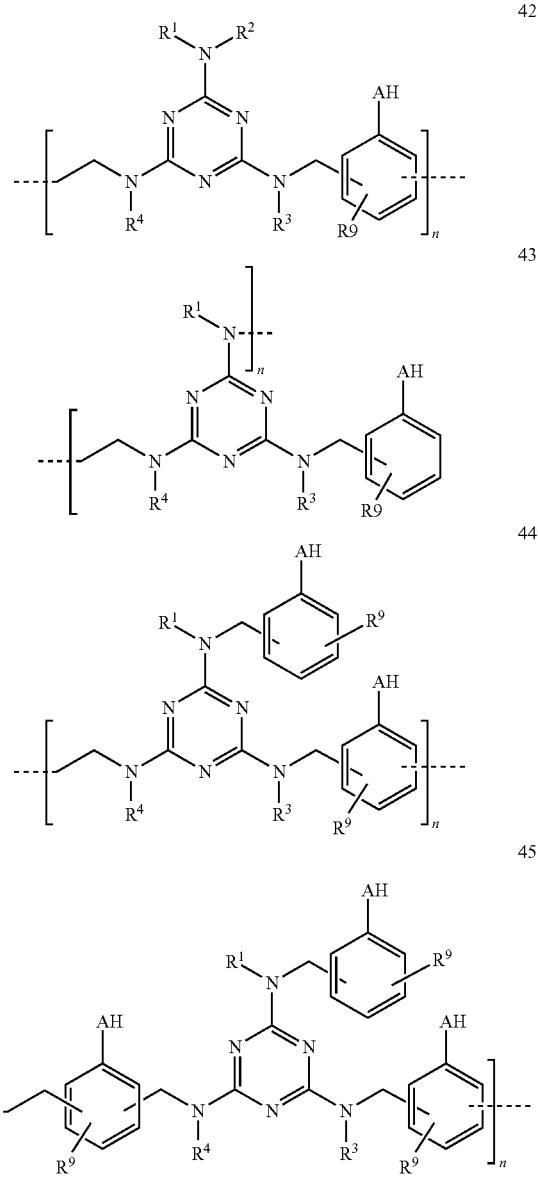

wherein n is larger than 1 and
wherein $R^1$, $R^2$, $R^3$, $R^4$, and A have the above meanings.

15. The process according to claim 8, wherein step a) is carried out at a pH between 9 and 11.

16. The process according to claim 8, wherein step a) is carried out in the presence of $K_2CO_3$, $Na_2CO_3$, $Ca(OH)_2$, NaOH and/or KOH.

17. The process according to claim 8, wherein steps b) and c) are carried out at a pH between 2 and 5.

18. The process according to claim 8, wherein steps b) and c) are carried out at a pH between 2 and 4.

19. The process according to claim 9, wherein the catalyst used in steps b) and c) is selected from a group comprising sulphonic acid, sulphuric acid, trifluoracetic acid (TFAA), 4-toluenesulphonic acid (pTSA), monochloracetic acid (MCAA), glacial acetic acid, formic acid, hydrochloric acid and zeolithes.

20. The process according to claim 10, wherein steps b) and c) are carried out in benzol, chloroform, methylenehloride, acetic acid, formic acid, cresol, formalin or water.

21. The process according to claim 10, wherein steps b) and c) are carried out in phenol melt.

22. The precondensate according to claim 13, wherein the components further comprise at least one of phenol and/or melamine.

23. The precondensate according to claim 13, wherein the components further comprise at least one of phenol-formaldehyde-, melamine-formaldehyde- and/or urea-formaldehyde-precondensates.

24. The precondensate according to claim 14, wherein n is 1 to 50.

25. The precondensate according to claim 14, wherein n is 1 to 10.

* * * * *